US011406526B2

(12) United States Patent
Chen et al.

(10) Patent No.: US 11,406,526 B2
(45) Date of Patent: Aug. 9, 2022

(54) ORAL DEVICE TO ELIMINATE AIR SPACE IN ORAL CAVITY

(71) Applicant: Somnics, Inc. (Taiwan), Hsinchu (TW)

(72) Inventors: Chung-Chu Chen, Hsinchu (TW); Yin-Ruei Chen, Hsinchu (TW); Ming-Jian You, Hsinchu (TW); Wen-Yen Huang, Hsinchu (TW)

(73) Assignee: Somnics, Inc., Zhubei (TW)

( * ) Notice: Subject to any disclaimer, the term of this patent is extended or adjusted under 35 U.S.C. 154(b) by 0 days.

(21) Appl. No.: 14/153,336

(22) Filed: Jan. 13, 2014

(65) Prior Publication Data

US 2014/0190489 A1 Jul. 10, 2014

Related U.S. Application Data

(60) Provisional application No. 61/751,559, filed on Jan. 11, 2013.

(51) Int. Cl.
*A61F 5/56* (2006.01)

(52) U.S. Cl.
CPC .................... *A61F 5/566* (2013.01)

(58) Field of Classification Search
CPC ....... A61C 17/02; A61C 17/0208; A61C 5/14; A61C 7/04; A61C 7/043; A61M 16/0057; A61M 16/0463; A61M 16/0488; A61M 16/49; A61M 16/0493; A61M 16/497; A61F 5/56; A61F 5/566; A61F 2005/563
USPC .............. 128/848, 859–861, 201.26, 205.19, 128/205.24, 206.29, 207.14; 433/91, 93
See application file for complete search history.

(56) References Cited

U.S. PATENT DOCUMENTS 2,599,521 A * 6/1952 Berman ................... 128/207.14
2,937,445 A * 5/1960 Erickson .................. A61B 1/24
433/93
3,091,859 A 6/1963 Baughan
(Continued)

FOREIGN PATENT DOCUMENTS

CN 101143115 A 3/2008
EP 1 192 928 A2 * 4/2005
(Continued)

OTHER PUBLICATIONS

Colrain et al. "A Multi-Centre Evaluation of Oral Pressure Therapy for the Treatment of Obstructive Sleep Apnoea." SRI International, ApniCure, Inc. Abstract/Pamphlet.
(Continued)

*Primary Examiner* — Camtu T Nguyen
(74) *Attorney, Agent, or Firm* — Stinson LLP

(57) ABSTRACT

This invention provides devices and systems and methods therefrom for properly controlling negative pressure applied to oral cavity, facilitating breathing and treating sleep apnea and snoring. The systems comprise a negative pressure system providing a vacuum source and an oral device comprising a shield, a tube passing through the shield, a flexible negative pressure deliverable part connected to the shield or the tube, an optional tongue protector, where the negative pressure deliverable part is conformable to the contour of the upper palate. Negative pressure is delivered to the front and back zones inside the oral cavity via the negative pressure deliverable part to eliminate air space in the oral cavity.

33 Claims, 20 Drawing Sheets

(56) References Cited

U.S. PATENT DOCUMENTS

| | | | |
|---|---|---|---|
| 3,132,647 A | | 5/1964 | Comiello |
| 4,063,552 A | * | 12/1977 | Going et al. .................. 128/861 |
| 4,169,473 A | | 10/1979 | Samelson |
| 4,304,227 A | | 12/1981 | Samelson |
| 4,368,737 A | | 1/1983 | Ash |
| 4,669,459 A | | 6/1987 | Spiewak et al. |
| 4,676,240 A | | 6/1987 | Gardy |
| 5,050,616 A | | 9/1991 | Wolff |
| 5,094,616 A | * | 3/1992 | Levenson .............. A61C 17/08 433/93 |
| 5,104,315 A | | 4/1992 | McKinley et al. |
| 5,361,921 A | * | 11/1994 | Burns ................ B01L 3/50825 215/247 |
| 5,465,734 A | | 11/1995 | Alvarez et al. |
| 5,513,986 A | * | 5/1996 | Feltham et al. ................ 433/91 |
| 5,533,523 A | | 7/1996 | Bass, Jr. et al. |
| 5,588,836 A | | 12/1996 | Landis et al. |
| 5,692,523 A | * | 12/1997 | Croll .................... A63B 71/085 128/859 |
| 5,718,225 A | * | 2/1998 | Visveshwara et al. ... 128/200.26 |
| 5,876,199 A | * | 3/1999 | Bergersen ................ A61C 7/08 433/6 |
| 5,915,385 A | | 6/1999 | Hakimi |
| 5,957,131 A | | 9/1999 | Hart |
| 5,957,133 A | | 9/1999 | Hart |
| 6,186,783 B1 | * | 2/2001 | Brassil ................... A61C 17/08 433/91 |
| 6,494,209 B2 | | 12/2002 | Kulick |
| 6,679,257 B1 | | 1/2004 | Robertson et al. |
| 6,820,617 B2 | | 11/2004 | Robertson et al. |
| 6,877,513 B2 | | 4/2005 | Scarberry et al. |
| 6,955,172 B2 | | 10/2005 | Nelson et al. |
| 6,976,491 B2 | | 12/2005 | D'Agosto |
| 6,997,186 B2 | | 2/2006 | Robertson et al. |
| 7,073,505 B2 | | 7/2006 | Nelson et al. |
| 7,073,506 B2 | | 7/2006 | Robertson et al. |
| 7,182,082 B2 | | 2/2007 | Hoffrichter |
| 7,328,698 B2 | | 2/2008 | Scarberry et al. |
| 7,451,766 B2 | * | 11/2008 | Miller .............. A61M 16/0488 128/207.15 |
| 7,451,776 B2 | | 11/2008 | Miller |
| 7,918,222 B2 | * | 4/2011 | Chen ........................ 128/200.24 |
| 2001/0044593 A1 | | 11/2001 | Lundy |
| 2001/0047805 A1 | | 12/2001 | Scarberry et al. |
| 2003/0208149 A1 | | 11/2003 | Coffey |
| 2005/0166928 A1 | | 8/2005 | Jiang |
| 2005/0166929 A1 | | 8/2005 | Jiang |
| 2005/0217678 A1 | * | 10/2005 | McCormick ...... A61M 16/0841 128/206.29 |
| 2005/0236003 A1 | | 10/2005 | Meader |
| 2006/0096600 A1 | | 5/2006 | Witt et al. |
| 2006/0282010 A1 | | 12/2006 | Martin et al. |
| 2007/0277818 A1 | | 12/2007 | Chen |
| 2008/0188947 A1 | | 8/2008 | Sanders |
| 2008/0210244 A1 | | 9/2008 | Keropian |
| 2008/0216839 A1 | * | 9/2008 | Rutter ..................... 128/207.14 |
| 2008/0216843 A1 | | 9/2008 | Jiang |
| 2009/0120446 A1 | | 5/2009 | Vaska et al. |
| 2010/0147302 A1 | | 6/2010 | Selvarajan et al. |
| 2010/0268107 A1 | | 10/2010 | de Heer |
| 2010/0304324 A1 | | 12/2010 | Dragan |
| 2011/0073119 A1 | * | 3/2011 | Chen ....................... A61F 5/566 128/848 |
| 2011/0220124 A1 | * | 9/2011 | Vaska ............... A61M 16/0488 128/848 |
| 2011/0259346 A1 | | 10/2011 | Tsuiki et al. |
| 2012/0132215 A1 | | 5/2012 | Vaska et al. |
| 2013/0213409 A1 | | 8/2013 | Podmore et al. |
| 2014/0034064 A1 | * | 2/2014 | Chen ...................... A61F 5/566 128/848 |

FOREIGN PATENT DOCUMENTS

| | | | |
|---|---|---|---|
| EP | 1 913 968 | * | 4/2008 |
| EP | 1 913 968 A1 | * | 4/2008 |
| JP | 2008183388 A | | 8/2008 |
| TW | 318428 U | | 9/2007 |

OTHER PUBLICATIONS

Colrain et al. "A Multi-center Evaluation of Oral Pressure Therapy for the Treatment of Obstructive Sleep Apnea: Sleep architecture effects." SRI International, ApniCure, Inc. Abstract/Pamphlet.

Engelke et al. "Preliminary radiographic observations of the tongue-repositioning manoeuvre." *European Journal of Orthodontics*, 2006, 28:618-623, Oxford University Press.

Engelke et al. "Functional Treatment of Snoring Using Oral Shields in Conjunction with the Tongue Repositioning Manoevre." *Int. J. Odontostomat*, 2007, 1(2):133-139.

Engelke et al. "Functional treatment of snoring based on the tongue-repositioning manoeuvre." *European Journal of Orthodontics*, 2010, 32:490-495, Oxford University Press.

Lazard et al. "The Tongue-Retaining Device: Efficacy and Side Effects in Apnea Syndrome." *Journal of Clinical Sleep Medicine*, 2009, 5(5): 431-438.

Malhotra et al. "Oral Pressure Therapy Improves Obstructive Sleep Apnea." *Am J Respir Crit Care Med* 2012, Abstract.

Schwab et al. "Examining the mechanism of action of a new device using oral pressure therapy for the treatment of obstructive sleep apnoea," Sleep disordered breathing—Treatment, 21$^{st}$ Congress of the European Sleep Research Society, Paris, France, Sep. 8, 2012, Abstract.

Schwab et al. "Mechanism of Action of a Novel Device Using Oral Pressure Therapy (OPT) for the Treatment of OSA." Center for Sleep and Circadian Neurobiology, Univ. of Pennsylvania School of Medicine, Pamphlet.

Chinese Office action for Application No. 201480001034.0 with English translation, dated Sep. 2, 2015, 16 pages.

Chinese Notification of the Grant of the Patent Right for Application No. 201480001034.0 with English translation, dated May 24, 2016, 4 pages.

Taiwanese Office action for Application No. 103 101 121 with English translation, dated Dec. 7, 2015, 18 pages.

Taiwanese Notice of Allowance for Application No. 103 101 121 with English translation, dated May 24, 2016, 3 pages.

International Search Report for PCT Application No. PCT/US2014/011129, dated Jul. 17, 2014, 2 pages.

Australian Patent Examination Report No. 1 for Application No. 2014205191, dated Mar. 16, 2016, 3 pages.

Office action for U.S. Appl. No. 14/760,429, filed Sep. 22, 2107, 31 pages.

Final Office Action for U.S. Appl. No. 14/760,429, dated Apr. 26, 2018, 23 pages.

Final Office Action issued for U.S. Appl. No. 14/760,426 dated Nov. 23, 2018, 22 pages.

* cited by examiner

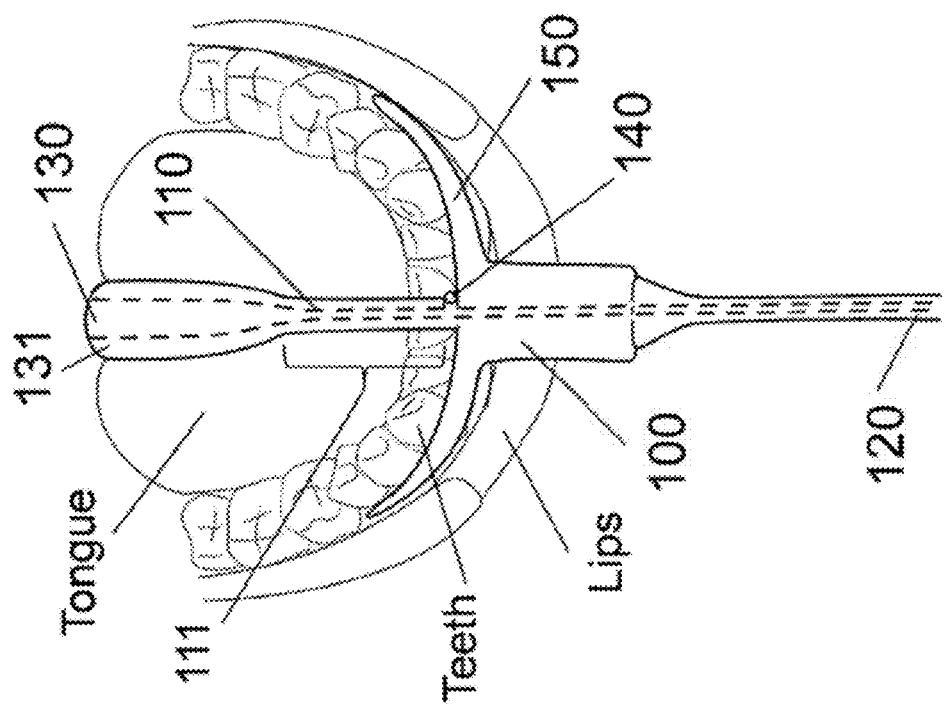
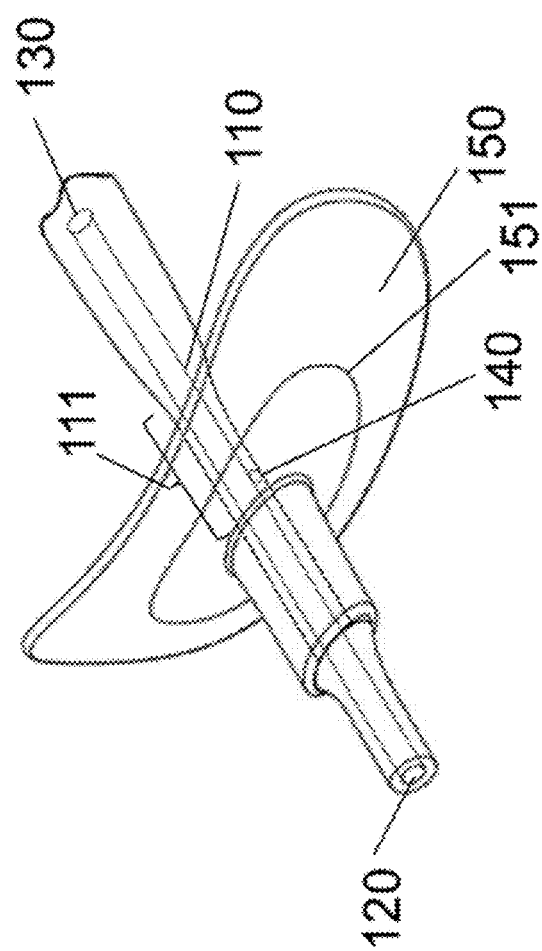
FIG. 2 (A)
FIG. 2 (B)

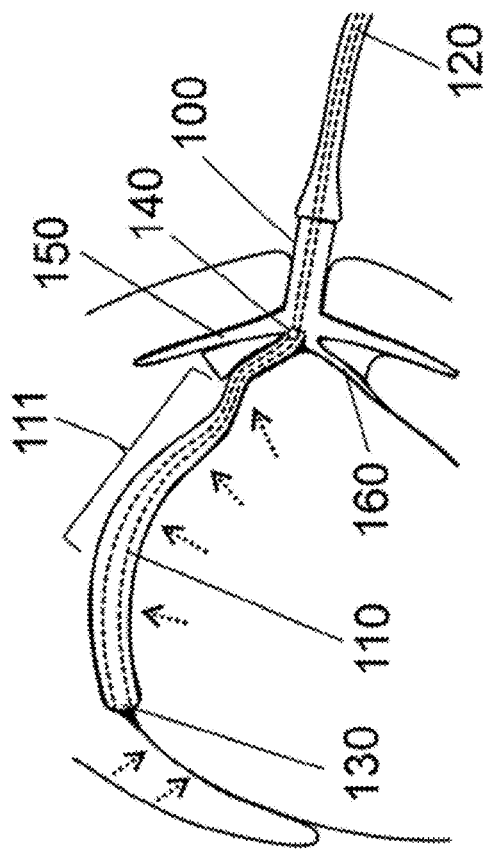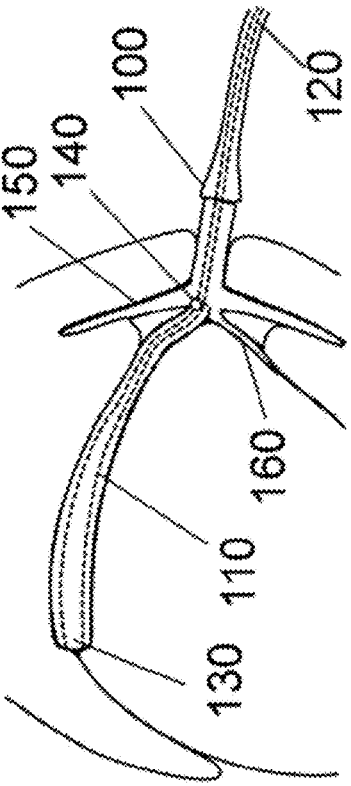
FIG. 3 (A)
FIG. 3 (B) Flatter Upper Palate
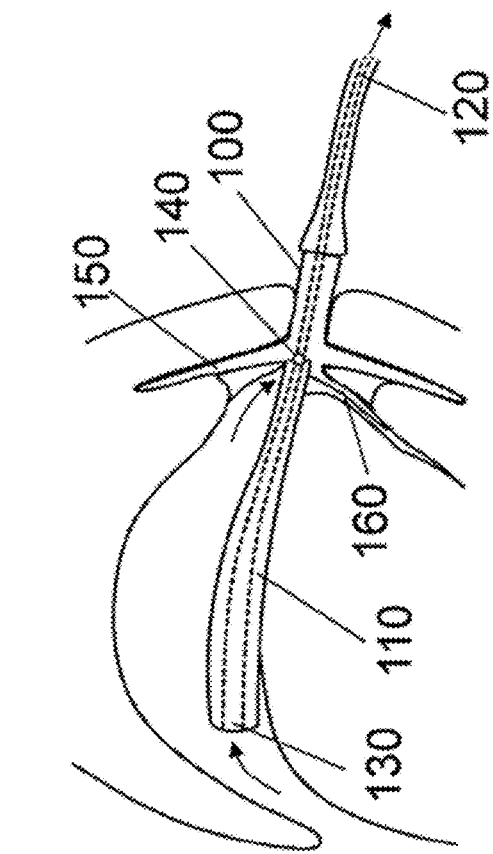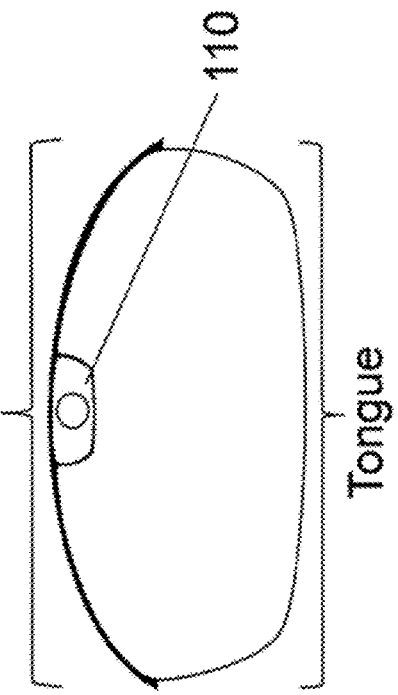
FIG. 3 (C)
FIG. 3 (D)

Inline lower Jaw

Forward lower Jaw

Backward lower Jaw

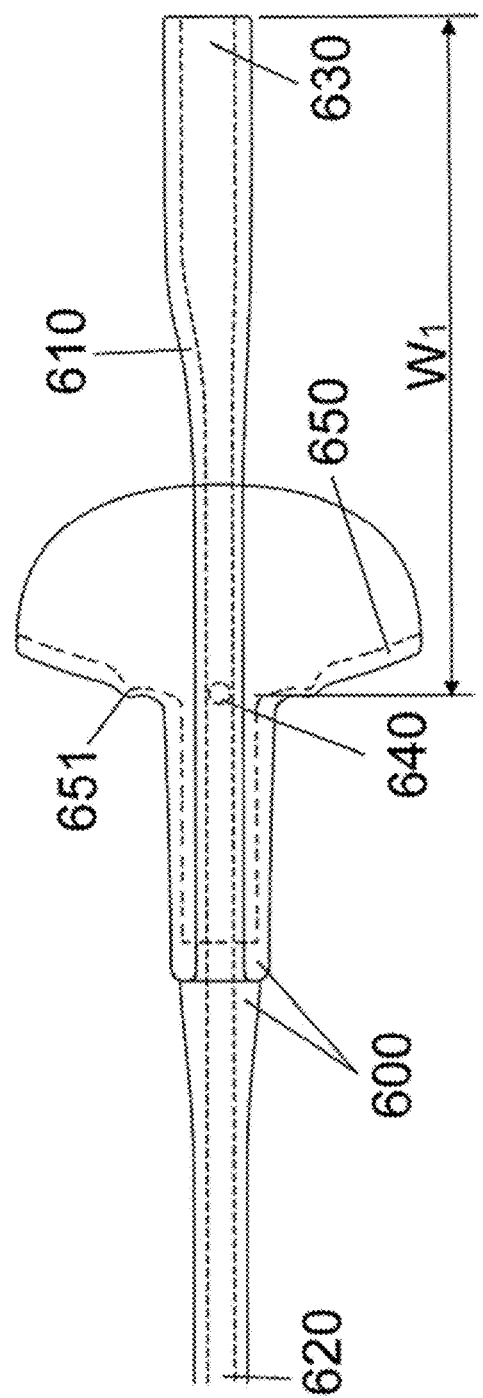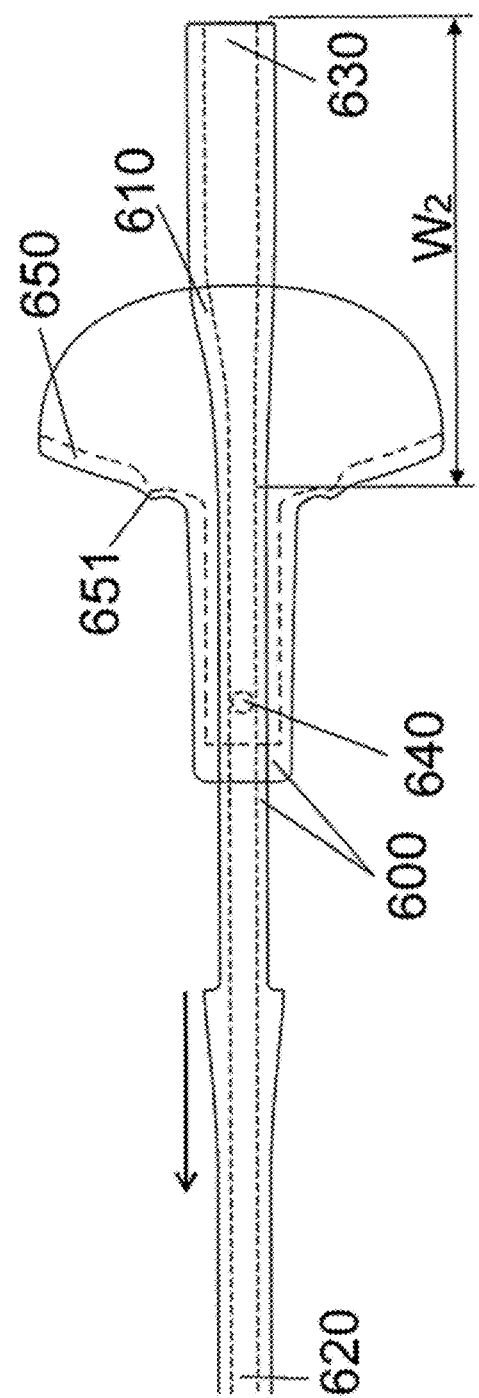
FIG. 9 (A)
FIG. 9 (B)

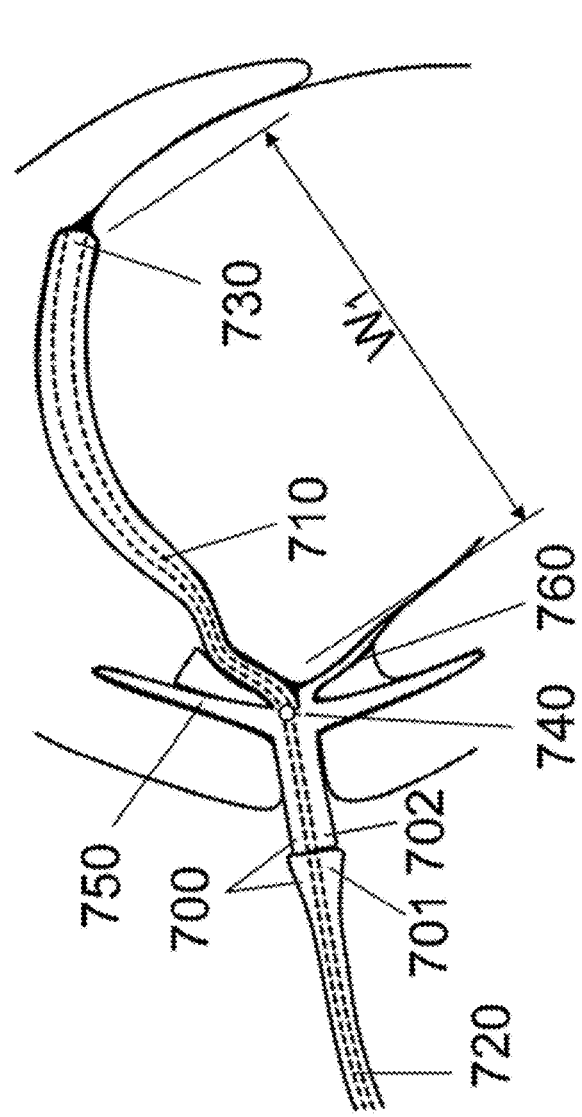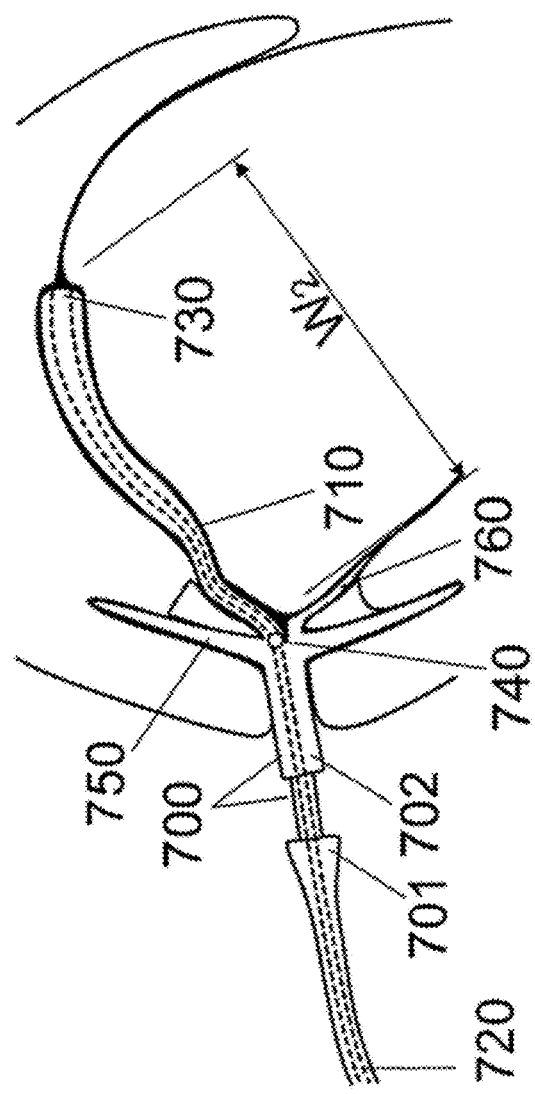
FIG. 10 (A)
FIG. 10 (B)

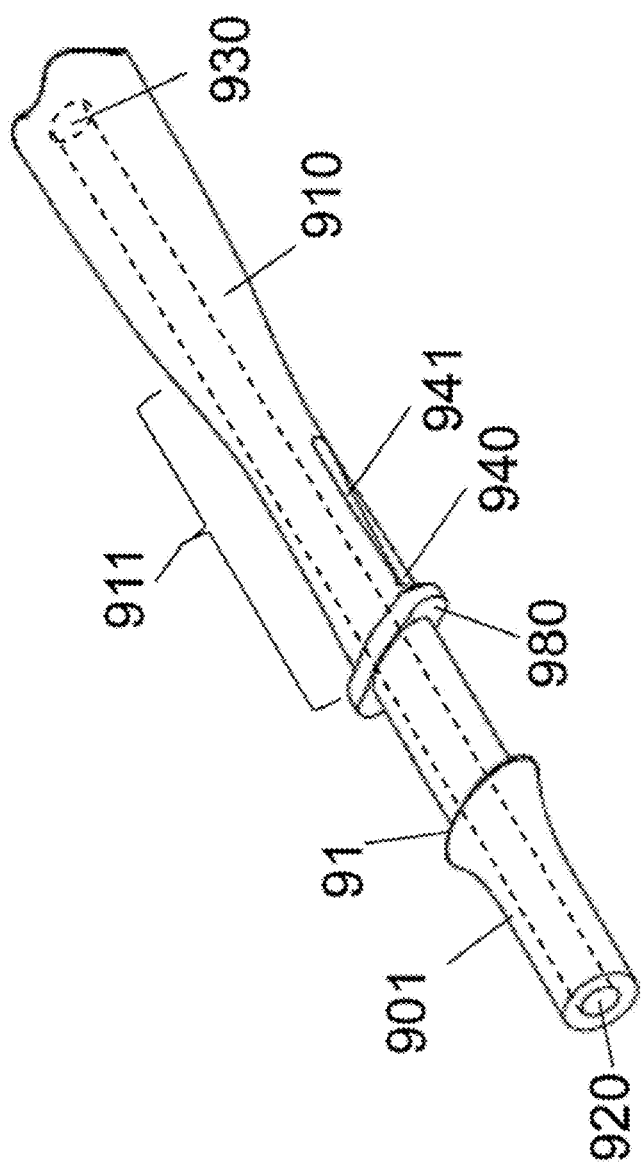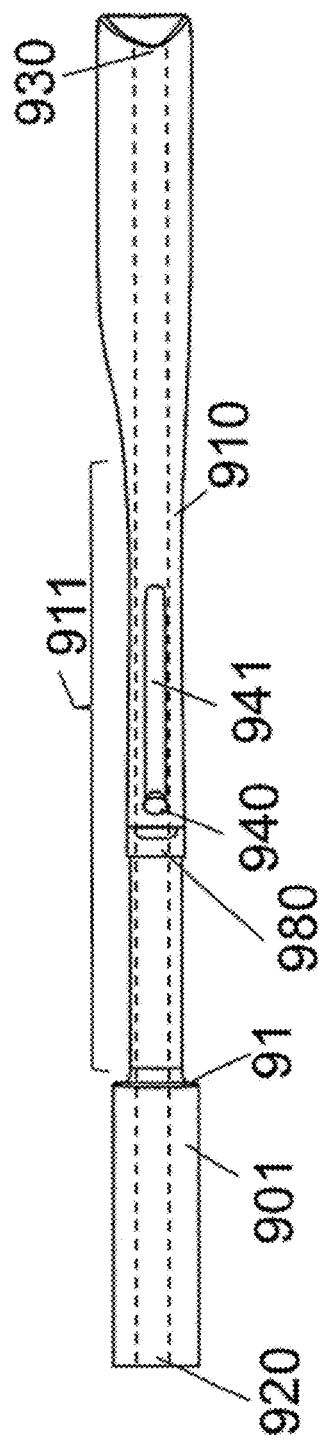
FIG. 12 (A)
FIG. 12 (B)

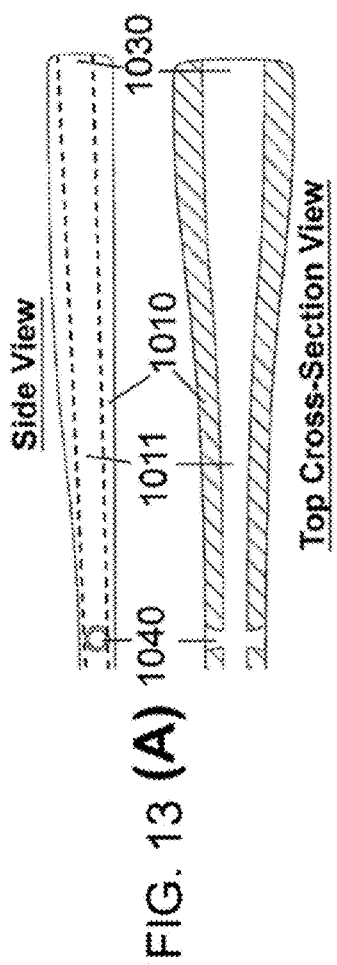
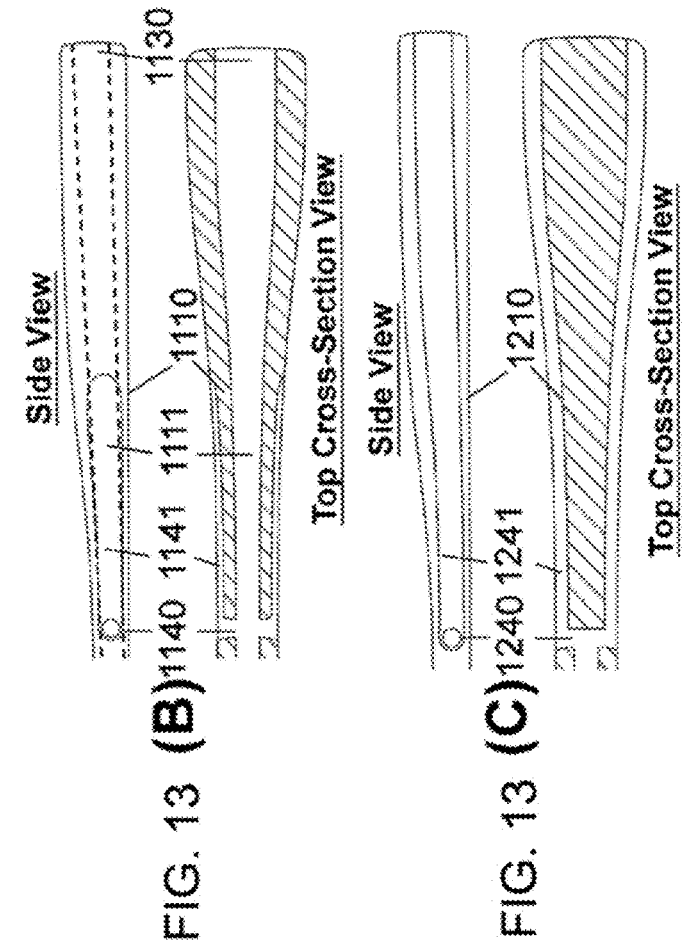

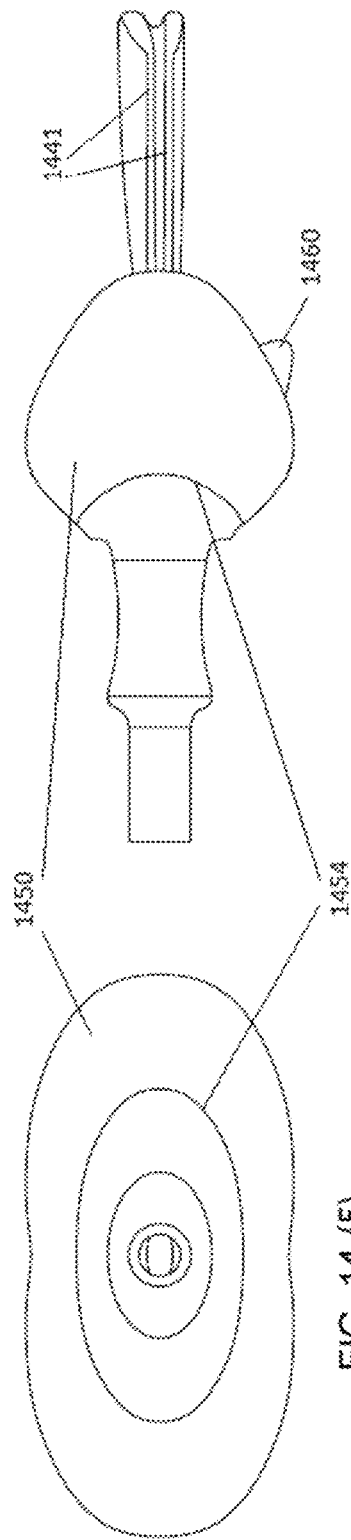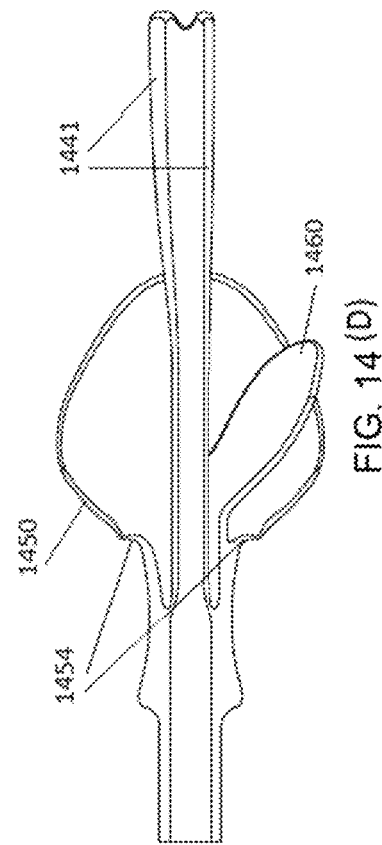

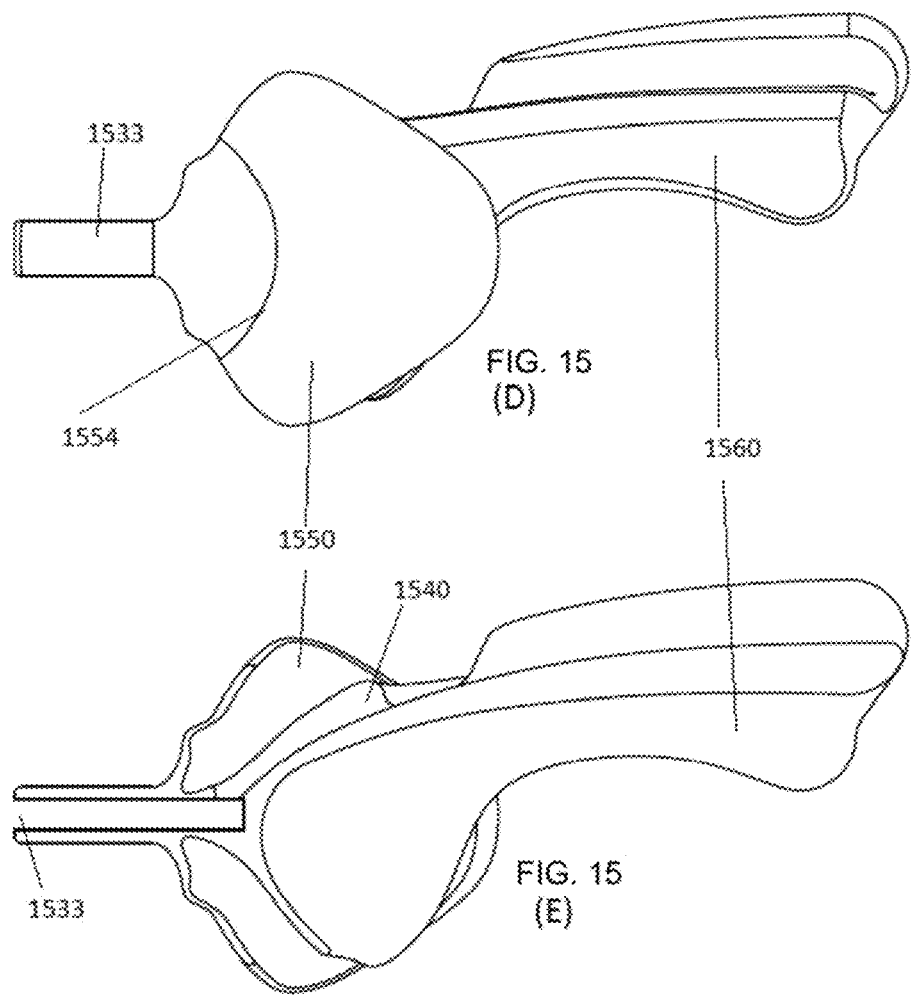

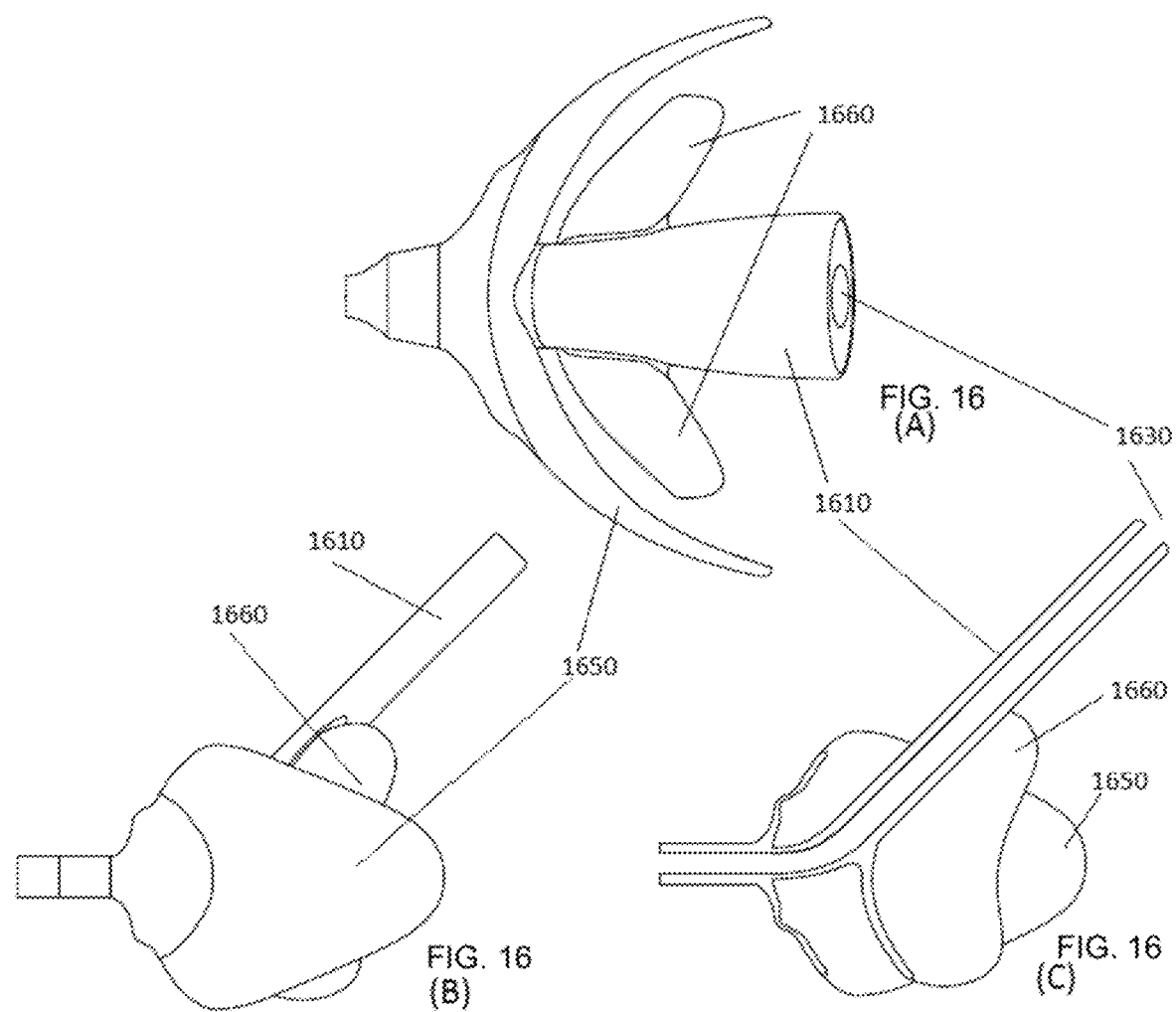

ORAL DEVICE TO ELIMINATE AIR SPACE
IN ORAL CAVITY

CROSS-REFERENCE

The application claims the benefit of U.S. Provisional Application Ser. No. 61/751,559, filed on Jan. 11, 2013, which application is incorporated herein by reference.

BACKGROUND OF THE INVENTION

Obstructive sleep apnea (OSA), hypopnea, and upper airway resistance syndrome (UARS) are among a variety of known disorders characterized by episodes of complete or partial upper airway obstruction during such as sleep, anesthetization, or post anesthesia. OSA, hypopnea, and UARS cause intermittent interruption of ventilation during sleep with the consequence of potentially severe oxyhemoglobin desaturation. Typically, those afflicted with OSA, hypopnea, and/or UARS experience repeated, frequent arousal from sleep in response to the oxygen deprivation. The arousals result in sleep fragmentation and poor sleep continuity.

SUMMARY OF THE INVENTION

In one aspect provides herein an oral device for eliminating air space in oral cavity comprising a shield situated between lips and front teeth, a tube passing through the shield, and a negative pressure deliverable part connected to the shield or the tube, wherein the negative pressure deliverable part is situated at the space between tongue and upper palate conformable to the contour of the upper palate, whereby the oral device delivers negative pressure via the negative pressure deliverable part to the oral cavity to eliminate air space between the tongue and the upper palate.

In some embodiments, the shield is flexible. In some embodiments, the shield comprises a bendable structure which is conformable to the shape of front teeth and lips. In some embodiments, the shield further functions as a seal. In some embodiments, the shield further comprises at least one air vent. In some embodiments, the at least one air vent is in place at positions that allow the lips cover the air vent. In certain embodiments, the air vent comprises a one-way vale. In certain embodiments, the flexible tube comprises 1-20 middle openings. In certain embodiments, the flexible tube comprises two middle openings.

In some embodiments, the negative pressure deliverable part comprises a flexible tube. In some embodiments, the flexible tube comprises an anterior end to connect to a vacuum source. In certain embodiments, the vacuum source is delivered by a negative control system. In some embodiments, the flexible tube comprises a bendable middle part, which is conformable to the contours of the upper palate and the tongue. In some embodiments, the middle part is thinner than the rest part of the tube. In some embodiments, the flexible tube has a wider structure near the posterior end to provide rigidity of the tube. In certain embodiments, the wider structure near the posterior end has a curved edge. In some embodiments, the oral device further comprises a tongue protector to prevent direct impingement of teeth on the tip of the tongue hi certain embodiments, the tongue protector is disposed between the bottom of the tongue tip and the back side of the lower front teeth. In certain embodiments, the tongue protector further comprises an indentation to accommodate the shape of tongue frenulum.

In some embodiments, the flexible tube and the shield are detachable. In some embodiments, the detachable shield part has an inner chamber to accommodate part of a bendable middle part of the detachable flexible tube part. In certain embodiments, the detachable tube part has an outer surface which contacts with an inner surface of the detachable shield part to form a sealing interface to maintain negative pressure environment within oral cavity. In certain embodiments, the detachable tube part and detachable shield part have different sizes and are interchangeable to accommodate different anatomy of patients. In some embodiments, the flexible tube is slidable. In certain embodiments, the oral device further comprises a shield with multiple anchor stops in different positions. In certain embodiments, the flexible tube further comprises open channels along the flexible tube. In some embodiments, the number of open channels is corresponding to the number of middle openings on the flexible tube. In certain embodiments, the flexible tube comprises two open channels on the flexible tube.

In some embodiments, the flexible tube comprises a bendable middle pan. In some embodiments, the bendable middle part is thinner than the rest part of the tube. In some embodiments, the tube has a wider structure than the rest of the tube near the posterior end. In certain embodiments, the structure near the posterior end has a curved edge. In certain embodiments, the open channels are extended to the posterior end of the flexible tubes. In certain embodiments, the section of the flexible tube having said open channels is solid. In certain embodiments, the flexible tube further comprises 1 to 20, 1 to 15, 1 to 10, or 1 to 7 support means to support the open channel from collapsing during the application of negative pressure.

In some embodiments, the negative pressure deliverable part comprises an extended tongue protector conformable the contour of the upper palate and is connected to the shield. In some embodiments, the extended tongue protector comprises at least one open channel. In some embodiments, the extended tongue protector is pre-shaped to conform the shape of upper palate. In some embodiments, the at least one open channel is connected to the at least one middle opening. In some embodiments, the tongue protector is integrated on the negative pressure deliverable part.

In another aspect provides herein an oral device for eliminating air space in oral cavity comprising a shield to be situated between lips and front teeth, and a tube passing through the shield, wherein the tube comprises a flexible negative pressure deliverable part to be situated at the space between tongue and upper palate conformable to the contour of the upper palate, whereby the oral device delivers negative pressure via the negative pressure deliverable part to the oral cavity to eliminate air space between the tongue and the upper palate. In some embodiments, the flexible negative pressure deliverable part further comprises at least one open channel along the flexible negative pressure deliverable part whereby the oral device delivers negative pressure via the negative pressure deliverable part and the at least one open channel to front and back of the oral cavity to eliminate air space between the tongue and the upper palate. In some embodiments, the shield has fold lines allowing the shield to be pliable and compliant to the tooth orientations and shapes. In some embodiments, the shield has recesses near the joint where the tube passing through allowing the tube to bend freely.

In another aspect provided herein are systems for eliminating air space in oral cavity comprising the invention oral device and a negative pressure control system providing a vacuum source. In some embodiments, the shield is flexible. In some embodiments, the shield comprises a bendable structure which is conformable to the shape of front teeth and lips. In some embodiments, the shield further functions as a seal. In some embodiments, the shield further comprises at least one air vent. In some embodiments, the at least one air vent is in place at positions that allow the lips cover the air vent. In certain embodiments, the air vent comprises a one-way vale. In certain embodiments, the flexible tube comprises 1-20 middle openings. In certain embodiments, the flexible tube comprises two middle openings. In some embodiments, the negative pressure deliverable part comprises a flexible tube. In some embodiments, the flexible tube comprises an anterior end to connect to a vacuum source. In certain embodiments, the vacuum source is delivered by a negative control system. In some embodiments, the flexible tube comprises a bendable middle part, which is conformable to the contours of the upper palate and the tongue. In some embodiments, the middle part is thinner than the rest part of the tube. In some embodiments, the flexible tube has a wider structure near the posterior end to provide rigidity of the tube. In certain embodiments, the wider structure near the posterior end has a curved edge. In some embodiments, the oral device further comprises a tongue protector to prevent direct impingement of teeth on the tip of the tongue. In certain embodiments, the tongue protector is disposed between the bottom of the tongue tip and the back side of the lower front teeth. In certain embodiments, the tongue protector further comprises an indentation to accommodate the shape of tongue frenulum. In some embodiments, the flexible tube and the shield are detachable. In some embodiments, the detachable shield pan has an inner chamber to accommodate part of a bendable middle pan of the detachable flexible tube part. In certain embodiments, the detachable tube part has an outer surface which contacts with an inner surface of the detachable shield part to form a sealing interface to maintain negative pressure environment within oral cavity. In certain embodiments, the detachable tube part and detachable shield part have different sizes and are interchangeable to accommodate different anatomy of patients. In some embodiments, the flexible tube is slidable. In certain embodiments, the oral device further comprises a shield with multiple anchor stops in different positions. In certain embodiments, the flexible tube further comprises open channels along the flexible tube. In some embodiments, the number of open channels is corresponding to the number of middle openings on the flexible tube. In certain embodiments, the flexible tube comprises two open channels on the flexible tube. In some embodiments, the flexible tube comprises a bendable middle part. In some embodiments, the bendable middle part is thinner than the rest part of the tube. In some embodiments, the tube has a wider structure than the rest of the tube near the posterior end. In certain embodiments, the structure near the posterior end has a curved edge. In certain embodiments, the open channels are extended to the posterior end of the flexible tubes. In certain embodiments, the section of the flexible tube having said open channels is solid. In certain embodiments, the flexible tube further comprises 1 to 20, 1 to 15, 1 to 10, or 1 to 7 support means to support the open channel from collapsing during the application of negative pressure. In some embodiments, the negative pressure deliverable part comprises an extended tongue protector conformable the contour of the upper palate and is connected to the shield. In some embodiments, the extended tongue protector comprises at least one open channel. In some embodiments, the extended tongue protector is pre-shaped to conform the shape of upper palate. In some embodiments, the at least one open channel is connected to the at least one middle opening. In some embodiments, the tongue protector is integrated on the negative pressure deliverable part.

In another aspect provided herein are methods for eliminating air space in oral cavity comprising attaching the invention oral device to the mouth of a patient; and applying a negative pressure by a negative control system on the middle openings and/or the posterior end of the flexible tube to both front and back of the oral cavity of the patient to eliminate air space between the tongue and the upper palate. In some embodiments, the shield is flexible. In some embodiments, the shield comprises a bendable structure which is conformable to the shape of front teeth and lips. In some embodiments, the shield further functions as a seal. In some embodiments, the shield further comprises at least one air vent. In some embodiments, the at least one air vent is in place at positions that allow the lips cover the air vent. In certain embodiments, the air vent comprises a one-way vale. In certain embodiments, the flexible tube comprises 1-20 middle openings. In certain embodiments, the flexible tube comprises two middle openings. In some embodiments, the negative pressure deliverable part comprises a flexible tube. In some embodiments, the flexible tube comprises an anterior end to connect to a vacuum source. In certain embodiments, the vacuum source is delivered by a negative control system. In some embodiments, the flexible tube comprises a bendable middle part, which is conformable to the contours of the upper palate and the tongue. In some embodiments, the middle part is thinner than the rest part of the tube. In some embodiments, the flexible tube has a wider structure near the posterior end to provide rigidity of the tube. In certain embodiments, the wider structure near the posterior end has a curved edge. In some embodiments, the oral device further comprises a tongue protector to prevent direct impingement of teeth on the tip of the tongue. In certain embodiments, the tongue protector is disposed between the bottom of the tongue tip and the back side of the lower front teeth. In certain embodiments, the tongue protector further comprises an indentation to accommodate the shape of tongue frenulum. In some embodiments, the flexible tube and the shield are detachable. In some embodiments, the detachable shield part has an inner chamber to accommodate part of a bendable middle part of the detachable flexible tube part. In certain embodiments, the detachable tube part has an outer surface which contacts with an inner surface of the detachable shield part to form a sealing interface to maintain negative pressure environment within oral cavity. In certain embodiments, the detachable tube part and detachable shield part have different sizes and are interchangeable to accommodate different anatomy of patients. In some embodiments, the flexible tube is slidable. In certain embodiments, the oral device further comprises a shield with multiple anchor stops in different positions. In certain embodiments, the flexible tube further comprises open channels along the flexible tube. In some embodiments, the number of open channels is corresponding to the number of middle openings on the flexible tube. In certain embodiments, the flexible tube comprises two open channels on the flexible tube. In some embodiments, the flexible tube comprises a bendable middle part. In some embodiments, the bendable middle part is thinner than the rest part of the tube. In some embodiments, the tube has a wider structure than the rest of the tube near the posterior end. In certain embodiments, the structure near the posterior end has a curved edge. In certain embodiments, the open channels are extended to the posterior end of the flexible tubes. In certain embodiments, the section of the flexible tube having said open channels is solid. In certain embodiments, the flexible tube further comprises 1 to 20, 1 to 15, 1 to 10, or 1 to 7 support means to support the open channel from collapsing during the application of negative pressure. In some embodiments, the negative pressure deliverable part comprises an extended tongue protector conformable the contour of the upper palate and is connected to the shield. In some embodiments, the extended tongue protector comprises at least one open channel. In some embodiments, the extended tongue protector is pre-shaped to conform the shape of upper palate. In some embodiments, the at least one open channel is connected to the at least one middle opening. In some embodiments, the tongue protector is integrated on the negative pressure deliverable part.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIGS. 2A and 2B show isometric and top views, respectively, of an exemplary oral device having a flexible tube conformable to the contour of the upper palate to eliminate air space in a patient's oral cavity during sleep.

FIGS. 3A-3D illustrate another aspect of the present invention showing various views of an exemplary oral device. FIGS. 3A and 3B show side views of an oral device having a flexible tube without and with negative pressure applied, respectively. FIG. 3C shows front cross-section view of an oral device having a flexible tube conformable to the contour of the upper palate with air space between tongue and soft palate eliminated. FIG. 3D shows side view of an oral device having a flexible tube conformable to a flatter upper palate with air space between tongue and soft palate eliminated.

FIG. 6A shows side cross-section view of an exemplary detachable tube part. FIG. 6B shows side cross-section view of an exemplary detachable shield part. FIG. 6C shows isometric, view of an exemplary detachable shield part. FIG. 6D shows side cross-section view of an exemplary oral device having a detachable flexible tube and a detachable shield.

FIGS. 7A and 7B show the side and side cross-section views of an exemplary detachable shield part with a tongue protector, respectively. FIG. 7C is a top view. FIG. 7D is a front view.

FIGS. 9A and 9B show side cross-section views of an oral device having a slidable flexible tube in original position and forward position, respectively.

FIGS. 10A and 10B show side cross-section views of an oral device having a slidable flexible tube in original position and forward position, respectively, with air space between tongue and soft palate eliminated.

FIGS. 12A and 12B show isometric and side views of a detachable flexible tube with open channels, respectively.

FIGS. 13A-13E show side cross-section views of variations of flexible tubes including tubes without opening at the posterior end with various open channels.

FIG. 14A is a top cross-section view. FIG. 14B is a top view. FIG. 14C is a side view. FIG. 14D is a side cross-section view. FIG. 14E is a front view. FIG. 14F is a rear view.

FIG. 15A is a top view. FIG. 15B is a front view. FIG. 15C is a rear view. FIG. 15D is a side view. FIG. 15E shows a side cross-section view.

FIG. 16A is a top view. FIG. 16B is a side view. FIG. 16C is a side cross-section view. FIG. 16D is a front view. FIG. 16E shows a rear view of an exemplary oral device.

DETAILED DESCRIPTION OF THE INVENTION

Figure 1:
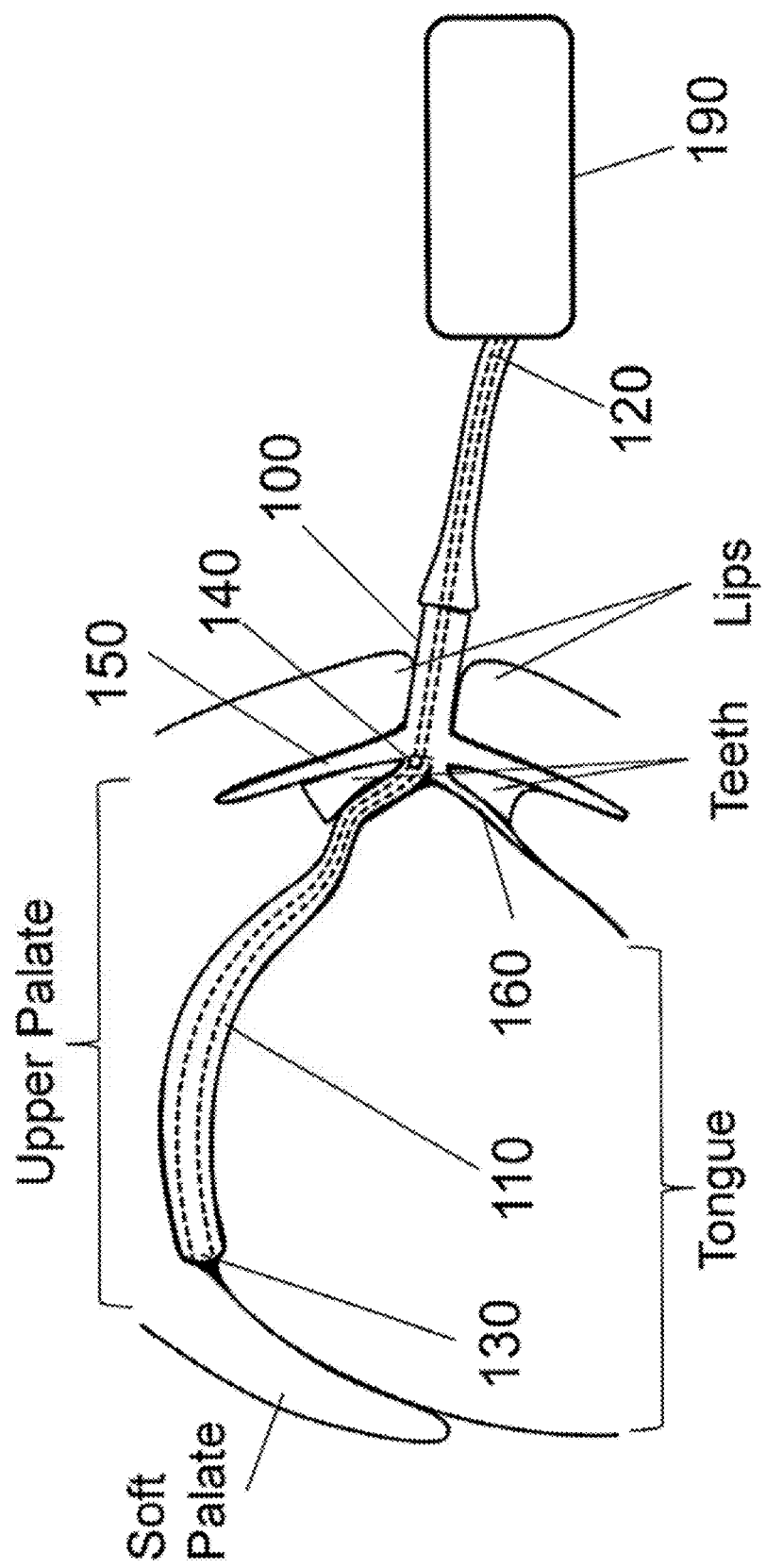
FIG. 1 illustrates one aspect of the present invention showing schematic diagrams of an exemplary system with an oral device comprising a negative pressure deliverable part (e.g., a flexible tube) conformable to the contour of the upper palate to eliminate air space in a patient's oral cavity during sleep.

Oral and external devices for treating sleep apnea and snoring have been disclosed in several publications utilizing several theories. It has been proposed to apply a negative pressure to the forward end of the patient's mouth, typically at or just behind the lips, to pull the tongue forward in order to lift the rear portion of the tongue away from the back of the airway. For example, an oral device for treatment of obstructive sleep disorders is characterized in that the tongue is protected and separated from the teeth when the device is in use. (See e.g., U.S. Pat. No. 4,304,227) The oral device further comprises a tongue shaped cavity for receiving the tongue where a negative pressure is applied directly on the soft tissues of the tongue to hold the tongue within the cavity. However, such negative pressure may cause damage to the soft tissues of the tongue.

Although various devices have been developed to facilitate breathing for those suffering from OSA, hypopnea or UARS by using oral negative pressure, to properly control negative pressure applied to oral cavity remains problematic.

The present invention provides devices and systems for properly controlling negative pressure applied to oral cavity, facilitating breathing and treating sleep apnea and snoring.

Reference will now be made in detail to the present exemplary embodiments, examples of which are illustrated in the accompanying drawings. Wherever possible, the same reference numbers are used in the drawings and the description to refer to the same or like parts.

Referring to FIG. 1, a schematic diagram of an exemplary invention system comprising a negative pressure control system 190 and an oral device 100 comprising a negative pressure deliverable part (e.g., a flexible tube 110), an optional tongue protector 160, and a shield 150 is shown. The oral device 100 for placement in a patient's oral cavity comprises a shield 150 to be situated between lips and front teeth, where a tube 110 passes through the shield is connected to a portion flexible and conformable to the contour of the upper palate (i.e., a negative pressure deliverable part). The flexible tube 110 has an anterior end 120 connected the negative pressure control system 190 which provides a vacuum source and a posterior end 130 to be situated between tongue and upper palate. The flexible tube 110 further optionally has at least one middle opening 140 near the shield 150. In some embodiments, the flexible tube 110 has 1 to 20, 1 to 15, 1 to 10, 1 to 5, 1 to 3, or 1 to 2 middle openings. As shown in FIG. 1, the position of the middle opening 140, in some embodiments, is on the side of the tube where it has less chance to be blocked by the soft tissue in patient's oral cavity. In certain embodiments, the flexible tube 110 has two middle openings 140 positioned on the side of the tube. The flexible tube 110 delivers negative pressure to both front and back of the oral cavity to eliminate air space between the tongue and the upper palate. An ordinary skilled in the art would readily apply the suitable negative pressure control system providing, a vacuum source (e.g. by an electronic pump disclosed in US2009/0288660, which is incorporated herein by reference, or the like).

In some embodiments, the shield 150 also functions as a seal to facilitate proper control of negative pressure applied to oral cavity. An ordinary skilled in the art would readily appreciate that the proper control of negative pressure applied to oral cavity is achieved via the opening of the posterior end 130 and at least one middle opening 140 of the tube and optionally via the shield which functions as a seal.

FIGS. 2A and 2B further illustrate an exemplary oral device in accordance with FIG. 1. FIG. 2A illustrates an isometric view of an oral device 100 comprising a flexible tube 110 passing through a shield 150. In some embodiments, the shield 150 comprises a bendable structure 151, which is conformable to the shape of patient's front teeth and lips. In certain embodiments, the flexible tube 110 has a bendable middle part 111, which is conformable to the contours of the upper palate and the tongue. In some embodiments, the middle part 111 is thinner than the rest part of the tube. The flexible tube 110 has an anterior end 120 to connect to a vacuum source (e.g., via a negative pressure control unit) and a posterior end 130 in place at the space between the tongue and the upper palate. The optional middle opening 140 is shown in FIG. 2A near the center of the shield 150. FIG. 2B illustrates a top view of an exemplary oral device in accordance with the embodiment shown in FIG. 1. The shield 150 is disposed between the front teeth and the lips and the flexible tube 110, in some embodiments, is disposed along the center line of the tongue. The flexible tube 110, in some embodiments, has a wider structure 131 near the posterior end 130 to provide rigidity of the tube, which prevent from collapsing due to being compressed by the tongue and the upper palate.

Referring to FIGS. 3A-3D, exemplary methods and system employing the present invention are described. FIG. 3A shows the side views of an exemplary oral device comprising a flexible tube without applying negative pressure. An oral device 100 is placed in a patient's oral cavity. The oral device 100 has a negative pressure deliverable part (i.e., a flexible tube 110) disposed between the tongue and the upper palate. The shield 150 is disposed between the front teeth and the lips. The anterior end 120 of the oral device 100 is connected to a vacuum source. The posterior end 130 and optionally at least one middle opening 140 of the oral device 100 is disposed between the tongue and upper palate and near the middle part of the shield 150, respectively. With negative pressure applied through the oral device, air space between the tongue and the upper palate is reduced gradually. An ordinary skilled in the art would readily appreciate that the tube 110 acting as a negative pressure deliverable part is flexible to conform to any contours of the upper palate of patients. FIG. 3B illustrates the tongue is drawn forward and upward to push and deform the flexible tube 110 to conform to the contour of the upper palate by application of negative pressure via the optionally at least one middle opening 140 and via posterior end 130 which further eliminates air space between the tongue and the soft palate. FIG. 3C shows front cross-section view of an oral device having a flexible tube conformable to the contour of the upper palate in accordance with FIG. 3B where air space between tongue and soft palate is reduced. The flexible tube 110 has a minimal cross section and occupies very little space in the oral cavity. FIG. 3D shows a side view of an oral device having a flexible tube conformable to a flatter upper palate (compared to one shown in FIG. 3(B)) with air space between tongue and soft palate eliminated. In some embodiments, the flexible tube 111 further comprises a more bendable part 111 (see FIG. 3B) to accommodate different anatomy of upper palate of different patients. An ordinary skilled, in the art would readily recognize that the bendable part 111 is not limited to the particular section shown in FIG. 3B, but any part that is conformable to the contour of the upper palate.

Figure 4:
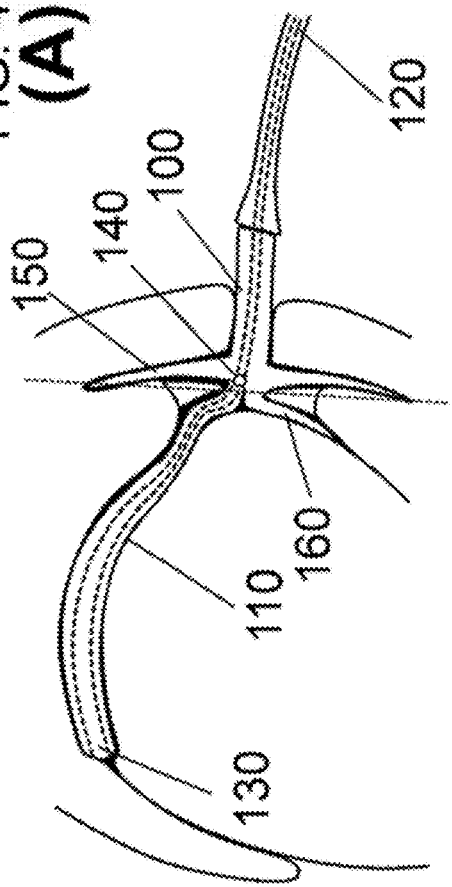
FIGS. 4A-4C show side views of an exemplary oral device having a flexible shield conformable to inline, backward, and forward lower jaws, respectively, with air space between tongue and soft palate eliminated.
Figure 4:
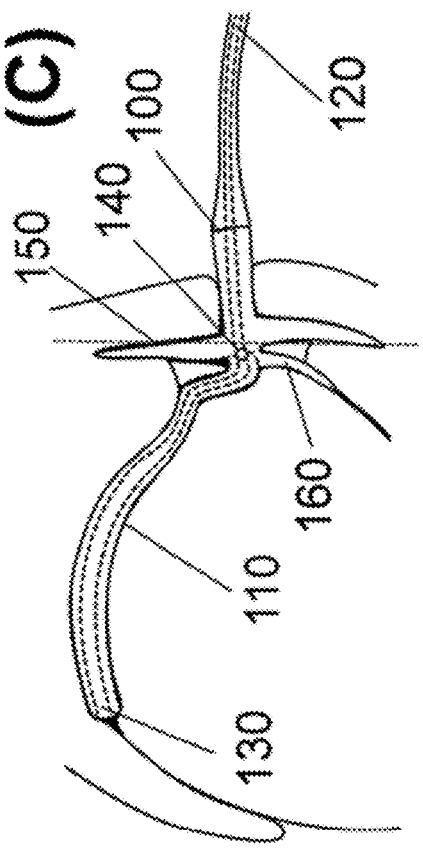
Figure 4:
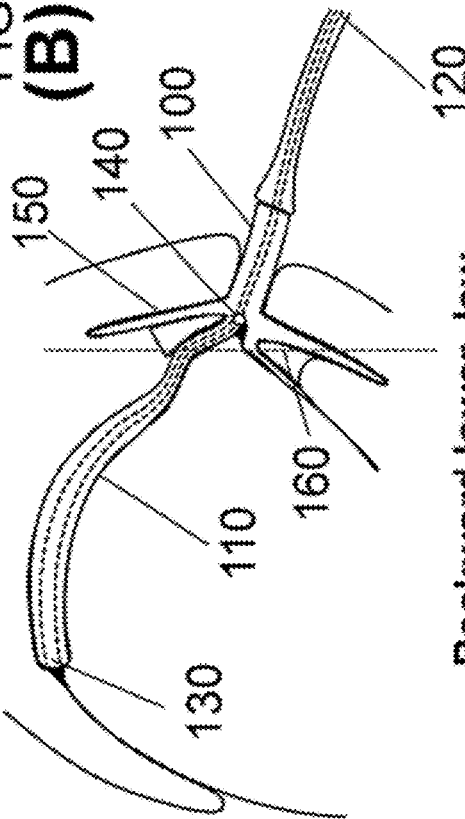

FIGS. 4A-4C illustrate a further variation of an oral device 100. FIG. 4A shows a side view of an oral device 100 comprising a flexible shield conformable to an inline lower jaw (in relative to upper jaw). The shield 150 is flexible and may further have a bendable structure (not shown), which can accommodate different anatomy of front teeth and lips of different patients, for patient with backward lower jaw e.g., as shown in FIG. 4B) and forward lower jaw (e.g., as shown in FIG. 4C), respectively.

Figure 5A:
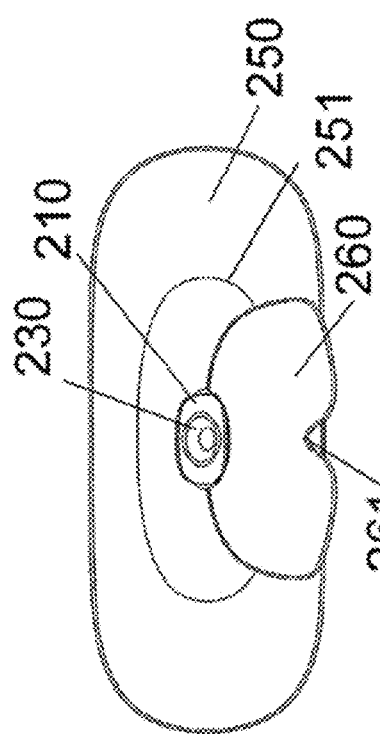
FIGS. 5A-5C illustrate another aspect of the present invention showing top, back, and side cross-section views, respectively, of an oral device having a flexible tube and a shield.
Figure 5B:
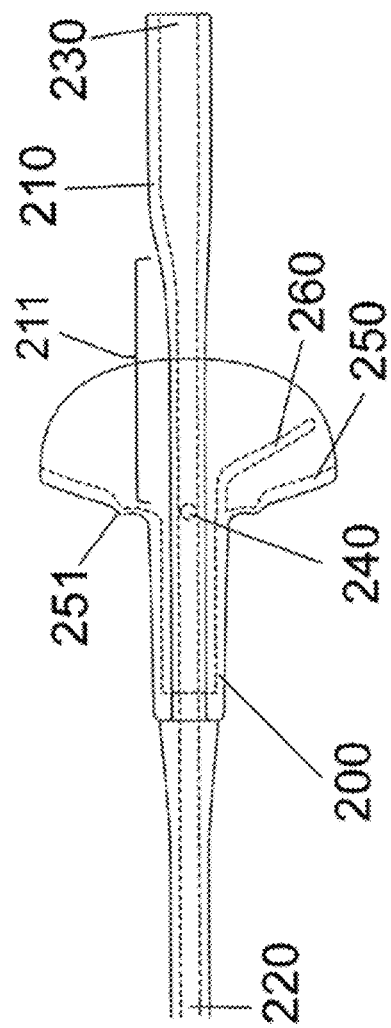
Figure 5C:
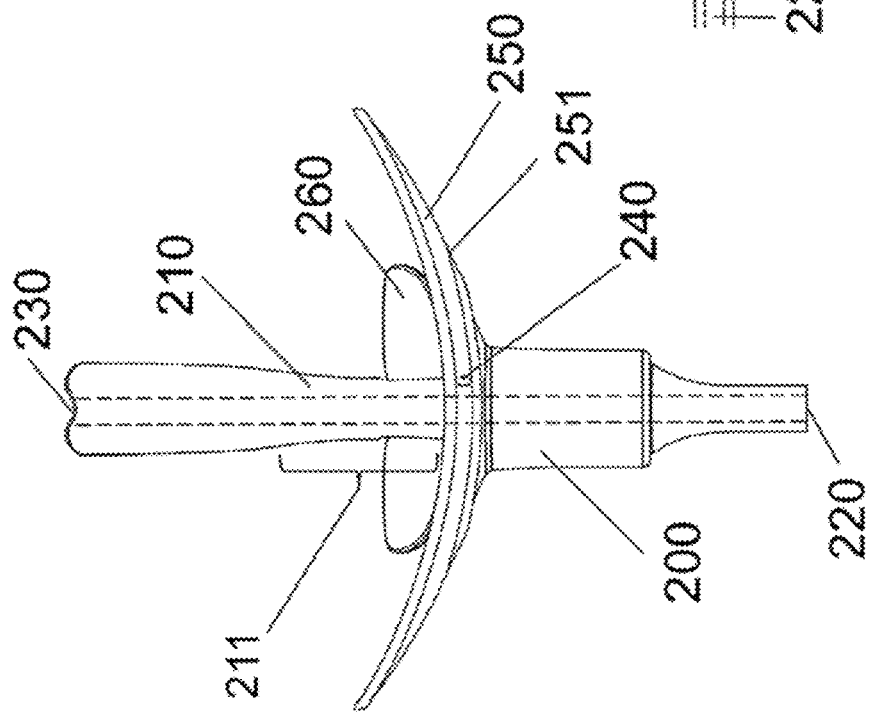

FIGS. 5A-5C illustrate another variation of invention oral devices showing top, back, and side cross-section views of an oral device 200 comprising a flexible tube 210 and a shield 250 where the flexible tube 210 passes through a shield 250. In some embodiments, the shield 250 has a bendable structure 251, which is conformable to the shape of from teeth and lips. The flexible tube 210, in some embodiments, further has a bendable middle part 211 (i.e., a negative pressure deliverable part), which is conformable to the contours of the upper palate and the tongue. Thus, in some embodiments, the tube passing through the shield is part of or directed connected to a flexible tube as described herein where the flexible tube functions as a negative pressure deliverable part. In certain embodiments, the middle part 211 is thinner than the rest part of the tube allowing more flexibility. In certain embodiments, the middle part 211 remains the same thickness as the rest part of the tube but still maintains the desired flexibility. An ordinary skilled in the art would readily realize it via the structure design (e.g., by a reinforced coating) or the material used (e.g., a more rigid produced material). In some embodiments, the material used to construct the middle part 211 is the same as the rest of the tube where the middle part is thinner than the rest of the tube. In certain embodiments, the material used to construct the middle part 211 is not the same as the rest of the tube and provides more flexible characteristic. The flexible tube 210, in some embodiments, has a wider structure near the posterior end 230 to provide rigidity of the tube, which prevent from collapsing due to being compressed by the tongue and the upper palate. In certain embodiments, the wider structure near the posterior end 230 has a curved edge. The flexible tube 210 has an anterior end 220 to connect to a vacuum source and a posterior end 230 in place at the space between the tongue and the upper palate. The flexible tube 210 further optionally has at least one middle opening 240 near the center of the shield 250. In some embodiments, the flexible tube 210 is one piece from the anterior end 220 to the posterior end 230. In some embodiments, the flexible tube 210 connects to a tube passing through the shield. In some embodiments, the oral device 200 further has a tongue protector 260 to prevent direct impingement of teeth on the tip of the tongue. The tongue protector 260 is disposed between the bottom of the tongue tip and the back side of the lower front teeth. In certain embodiments, the tongue protect 260 further has an indentation 261 to accommodate the shape of tongue frenulum.

Figure 6:
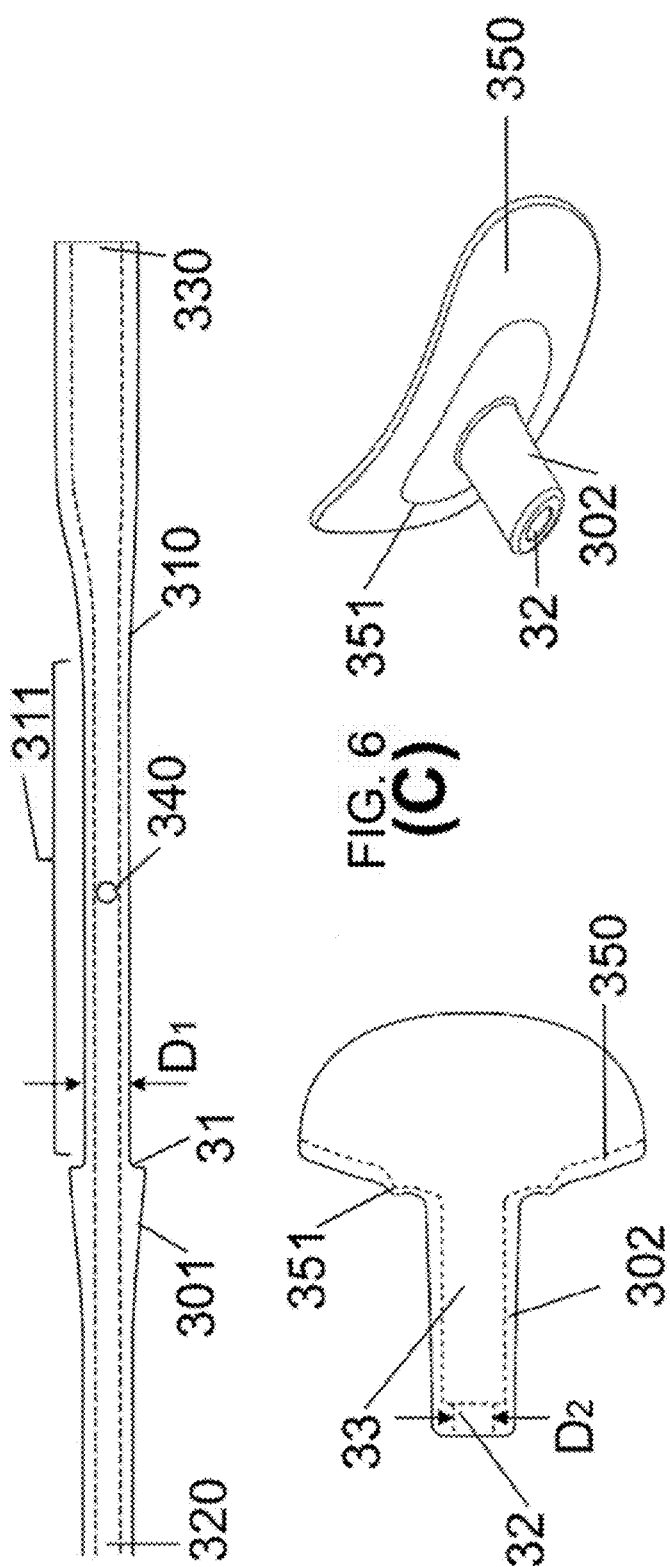
FIGS. 6A to 6D show various views of an exemplary oral device having a detachable flexible tube and a detachable shield.
Figure 6:
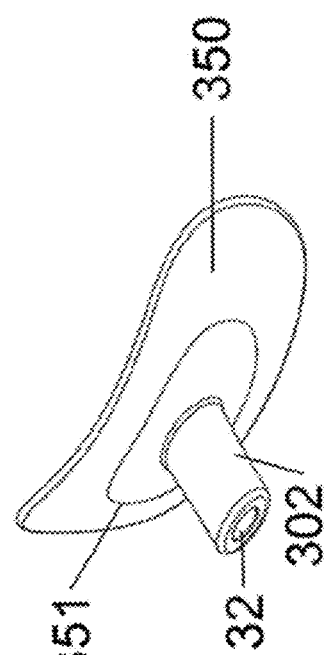
Figure 6:
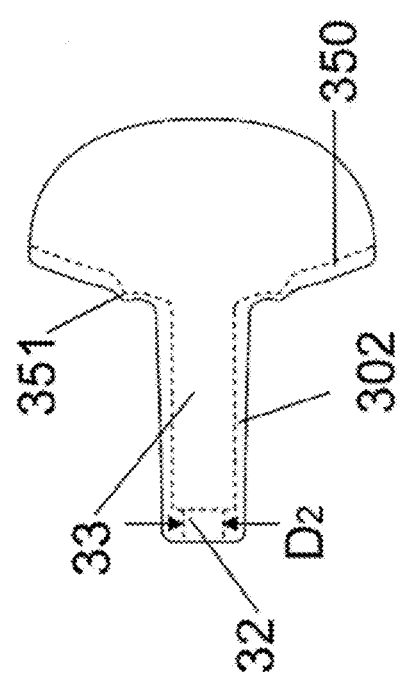
Figure 6:
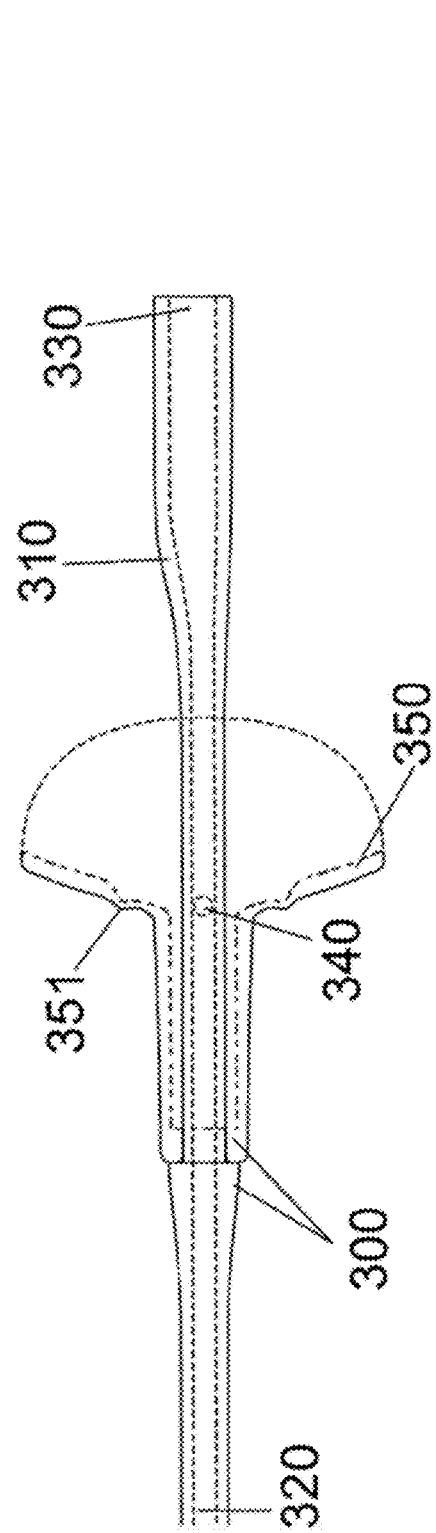

In some embodiments of the invention, there is provided an oral device 300 comprises a detachable tube part 301 and a detachable shield part 302 shown in various views in FIGS. 6A to 6D. FIG. 6A illustrates an exemplary detachable tube part 301 having a flexible tube 310 which is conformable to the contours of the upper palate and the tongue. In some embodiments, the flexible tube 310 comprises a bendable middle part 311. In certain embodiments, the middle part 311 is thinner than the rest part of the tube. In certain embodiments, the middle part 311 remains the same thickness as the rest part of the tube but still maintains the desired flexibility. An ordinary skilled in the art would readily recognize that to achieve the same flexibility by different thickness of the middle part 311, the material used, the shape, and/or the length of the middle part 311 need to be adjusted accordingly. The flexible tube 310, in some embodiments, has a wider structure near the posterior end 330 to provide rigidity of the tube, which prevent from collapsing due to being compressed by the tongue and the upper palate. In certain embodiments, the wider structure near the posterior end 330 has a curved edge. The flexible tube 310 has an anterior end 320 to connect to a vacuum source and a posterior end 330 in place at the space between the tongue and the upper palate. The flexible tube 310 further optionally has at least one middle opening 340 near the center of the shield 350 (see FIG. 6A and FIG. 6D). FIG. 6B illustrate a detachable shield part 302, having a shield 350 which comprises a bendable structure 351 being conformable to the shape of front teeth and the lips. The detachable shield part 302 has an inner chamber 33 (see FIG. 6B) to accommodate part of the bendable middle part 311 (see FIG. 6A) of the flexible tube 310. The detachable tube part 301 and detachable shield part 302 may have different sizes and are interchangeable to accommodate different anatomy of patients. In some embodiments, the detachable tube part 301 has an outer surface 31 (see FIG. 6A) which contacts with an inner surface 32 (see FIG. 6B/6C) of the detachable shield part 302 to form a sealing interface to maintain negative pressure environment within oral cavity. To ensure a good fit, the diameter of D1 should be corresponding to the diameter of D2. A complete assembly is shown in FIG. 6D.

Figure 7:
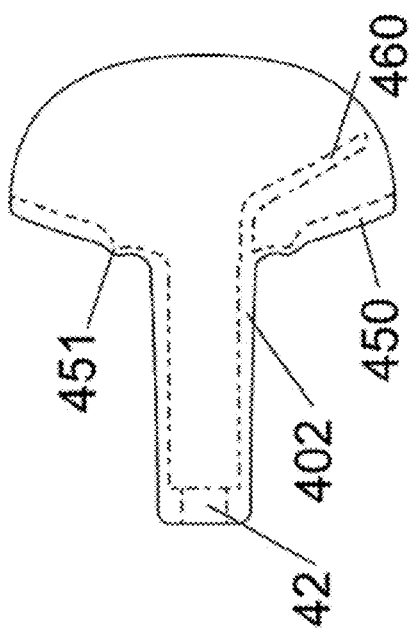
FIGS. 7A to 7D illustrate another aspect of the present invention showing various views of an exemplary detachable shield with a tongue protector.
Figure 7:
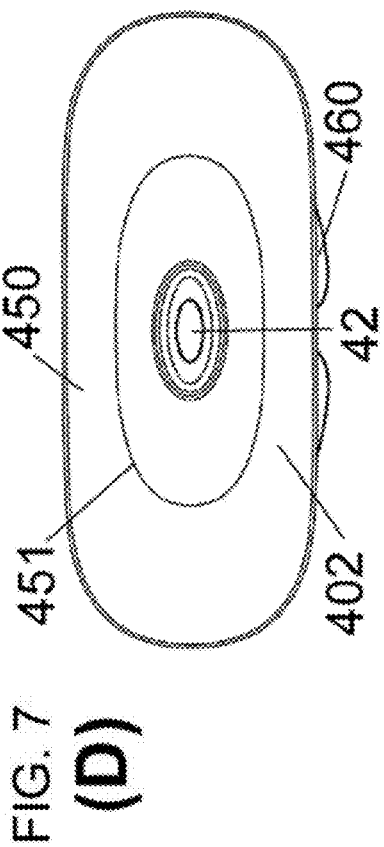
Figure 7:
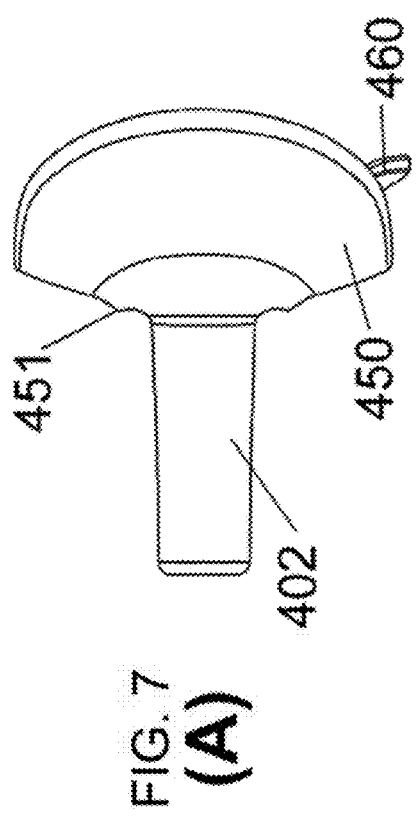
Figure 7:
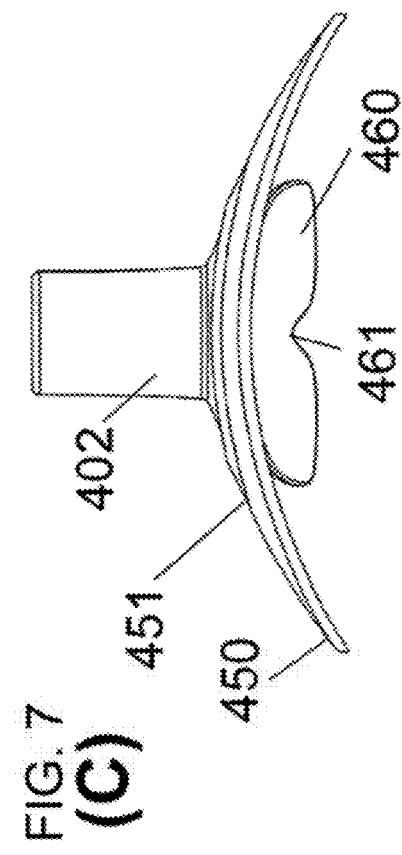

FIGS. 7A to 7D illustrate another embodiment of the invention showing various views of a detachable shield part 402 with a tongue protector 460 where the tongue protector 460 is disposed between the bottom of the tongue tip and the back side of the lower front teeth. FIG. 7A/B show the side-cross views of a detachable shield part 402 comprising a bendable middle part 451, a shield 450 and a tongue protector 460. In some embodiments, the detachable shield part 402 further comprises an inner surface 42 to accommodate a detachable tube part to form a sealing interface (see FIGS. 7B and 7D). In certain embodiments, the tongue protect 460 further comprises an indentation 461 (e.g., see FIG.7C) to accommodate the shape of tongue frenulum.

Figure 8:
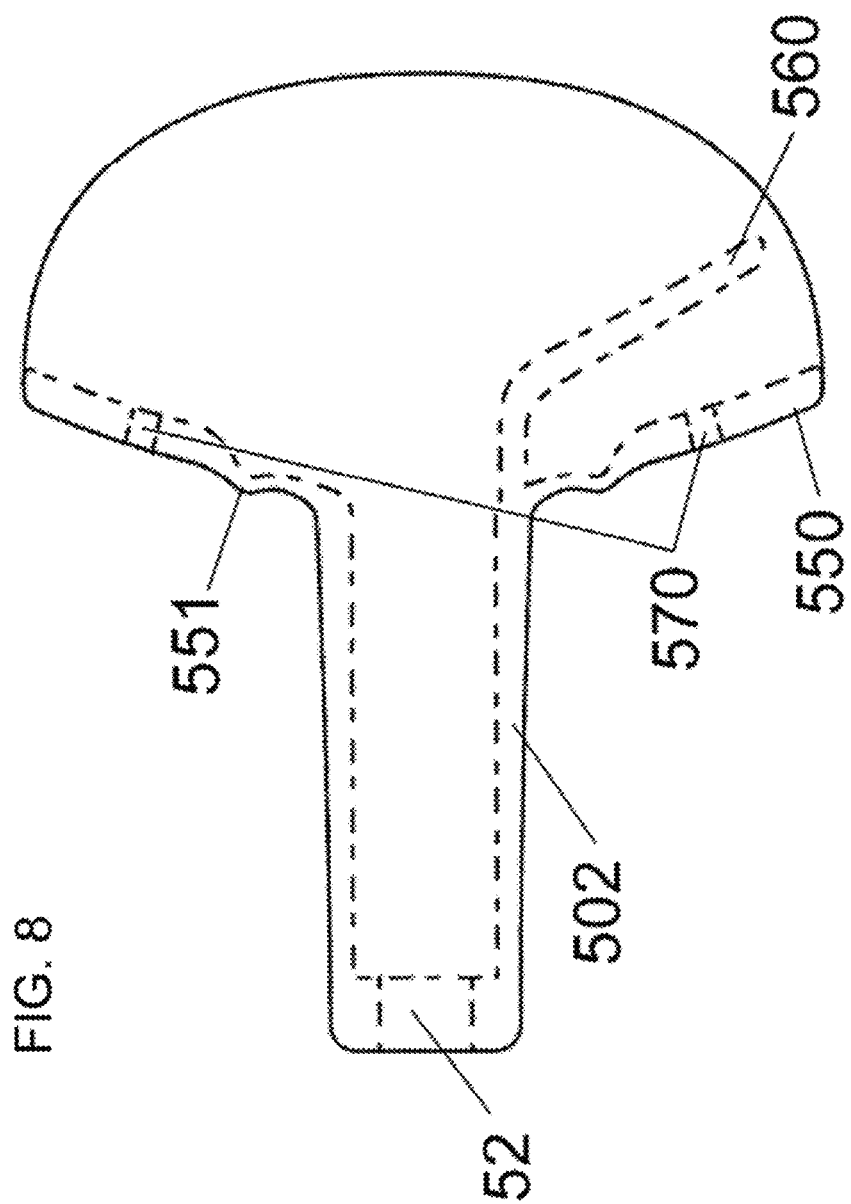
FIG. 8 illustrates another aspect of the present invention showing a side cross-section view of a detachable shield with air vents.

Referring to FIG. 8 shows the side cross-section view of a detachable shield part 502 comprising a tongue protector 560, a shield 550 and air vents 570 wherein the detachable shield part comprises a bendable middle part 551. The detachable shield part further comprises an inner surface 52 to accommodate a detachable tube part to form a sealing interface. The air vents 570 allow the patient to breathe more freely when the patient tries to open mouth or exhale through mouth. In some embodiments, the air vents comprise one-way vale to preserve the seal function of the detachable shield. A one-way vale restricts air entering from outside but allowing air to go out from the oral cavity. In some embodiments, the air vents are in place at positions that allow the lips to cover the air vents. For example, the air vents are positioned slightly above or below incisal face, where the air vents is in front of the upper front teeth or the bottom front teeth, and behind the lips.

Referring now to FIGS. 9A-9B, illustrate another aspect of the present invention showing an oral device 600 comprising a slidable flexible tube 610 in original position (W1, FIG. 9A) and forward position (W2, FIG. 9B), respectively. The oral device comprises a flexible tube 610 and a shield 650 comprising a bendable middle part 651 where the flexible tube 610 passes through the shield 650. The flexible tube 610 further optionally comprises at least one middle opening 640. The flexible tube 610 has an anterior end 620 to connect to a vacuum source and a posterior end 630 in place at the space between the tongue and the upper palate. The slidable flexible tube 610 allows a patient to adjust the position of the posterior end 630 to provide a more comfortable or effective location to deliver negative pressure between the tongue and the upper palate.

FIGS. 10A-10B show the side cross-section views of an oral device 700 comprising a slidable flexible tube 710 in original position (W1, FIG. 10A) and forward position (W2, FIG. 10B), respectively, with air space between tongue and soft palate eliminated. An oral device 700 is placed in a patient's oral cavity. The oral device 700 has a slidable flexible tube 710 disposed between the tongue and the upper palate. The shield 750 is disposed between the front teeth and the lips. The anterior end 720 of the oral device 700 is connected to a vacuum source (not shown). The posterior end 730 and at least one middle opening 740 of the oral device 700 is disposed between the tongue and upper palate and near the middle part of the shield 750, respectively. To accommodate the different anatomy of patients, the detachable tube part 701 can be moved away from the detachable shield part 702 which also move the position of the posterior end 730 forward. In certain embodiments, the posterior open end 730 is located anteriorly to the boundary between the hard palate and the soft palate, thus prevents the soft tissue on soft palate from blocking or being sucked into the posterior open end 730. The oral device 700 can further have as tongue protector 710 to prevent direct impingement of teeth on the tip of the tongue.

Figure 11:
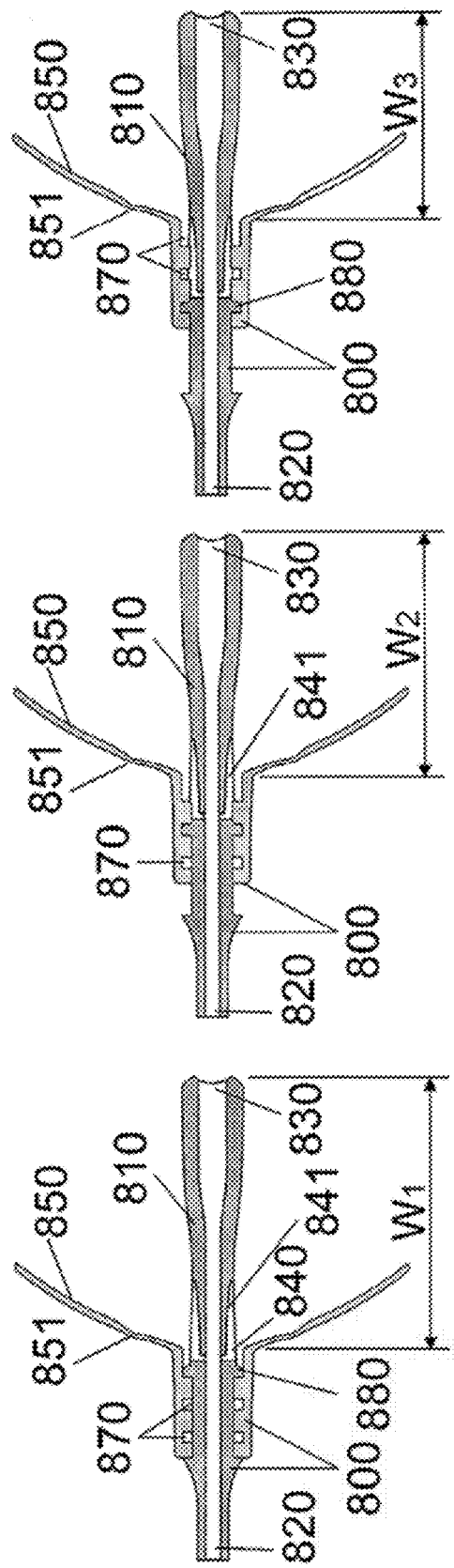
FIGS. 11A-11C show side cross-section views of an oral device having a slidable flexible tube with anchor points in different positions.
Figure 14:
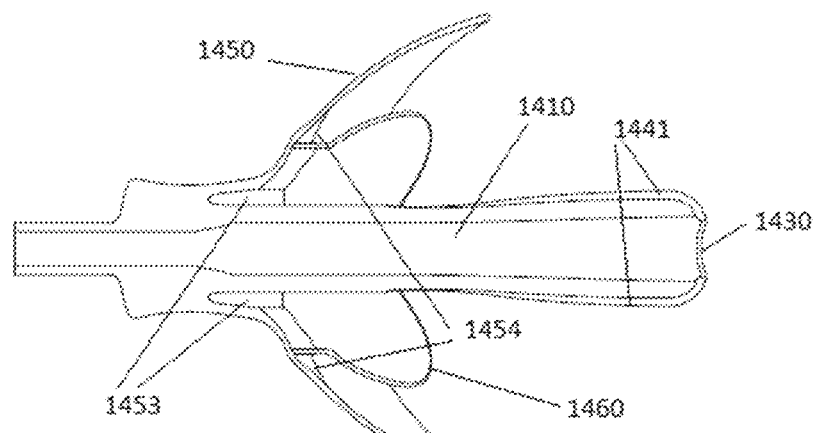
FIGS. 14A to 14F illustrate another aspect of the present invention showing various views of an exemplary oral device comprising open channels connecting with the posterior end without middle openings to deliver negative pressure from posterior part to anterior part of oral cavity.
Figure 14:
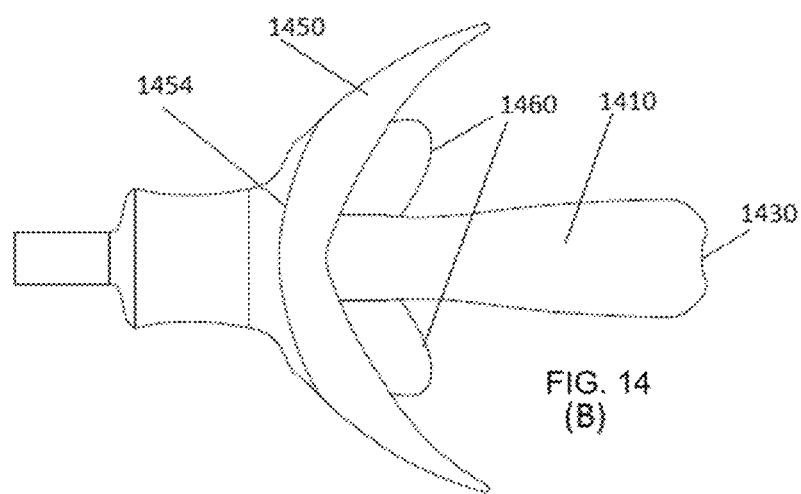
Figure 14F:
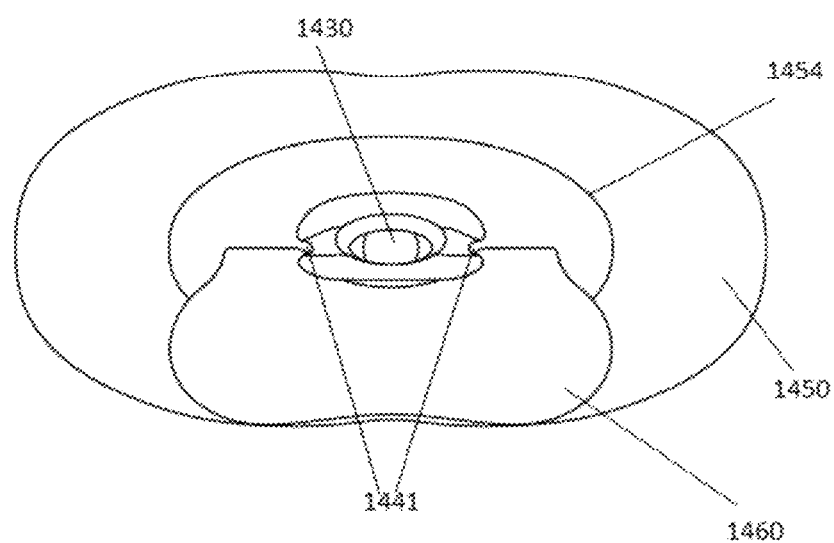
Figure 15:
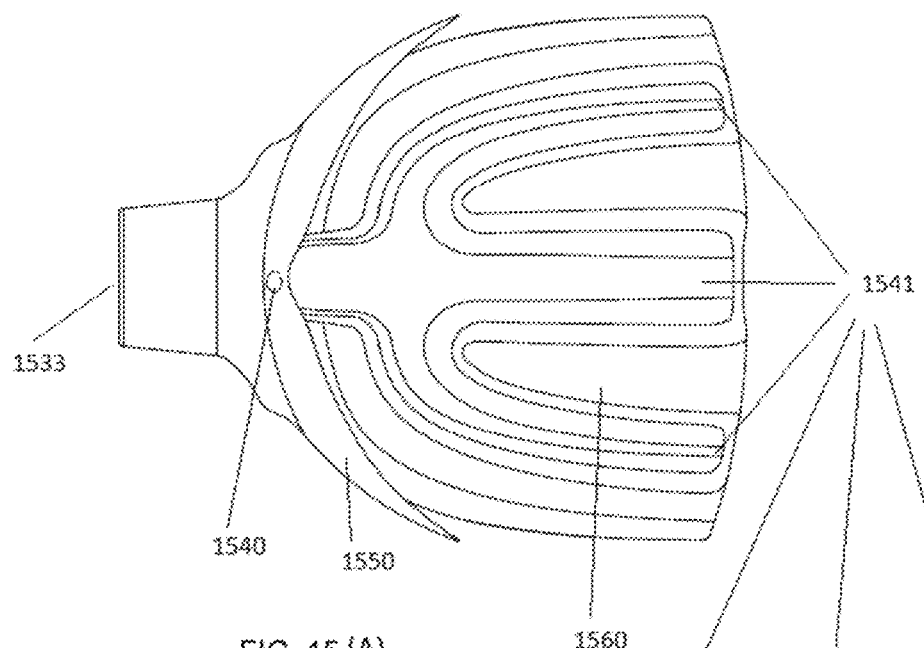
FIGS. 15A to 15E illustrate another aspect of the present invention showing various views of an exemplary oral device with extended tongue protector which combines the tongue protector described herein with the function of a flexible tube pre-shaped and conformable to the shape of the upper plate.
Figure 15:
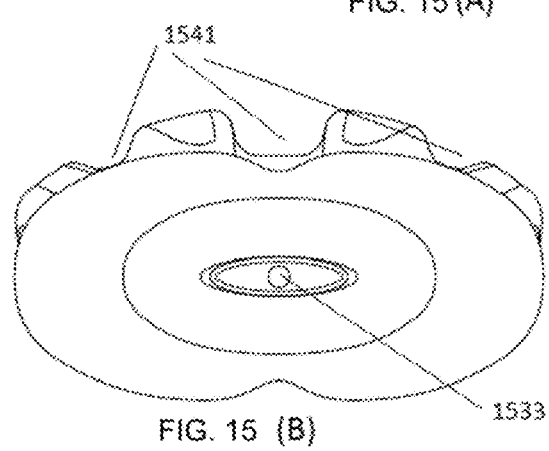
Figure 15:
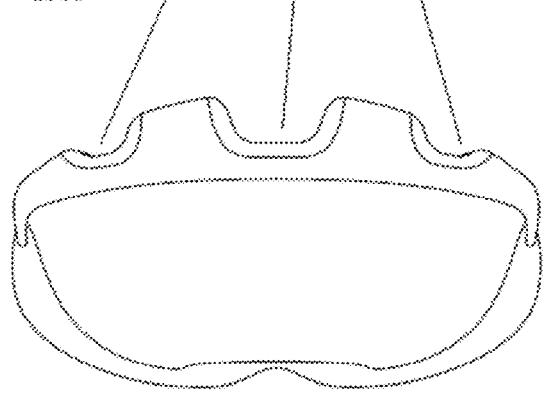
Figure 16:
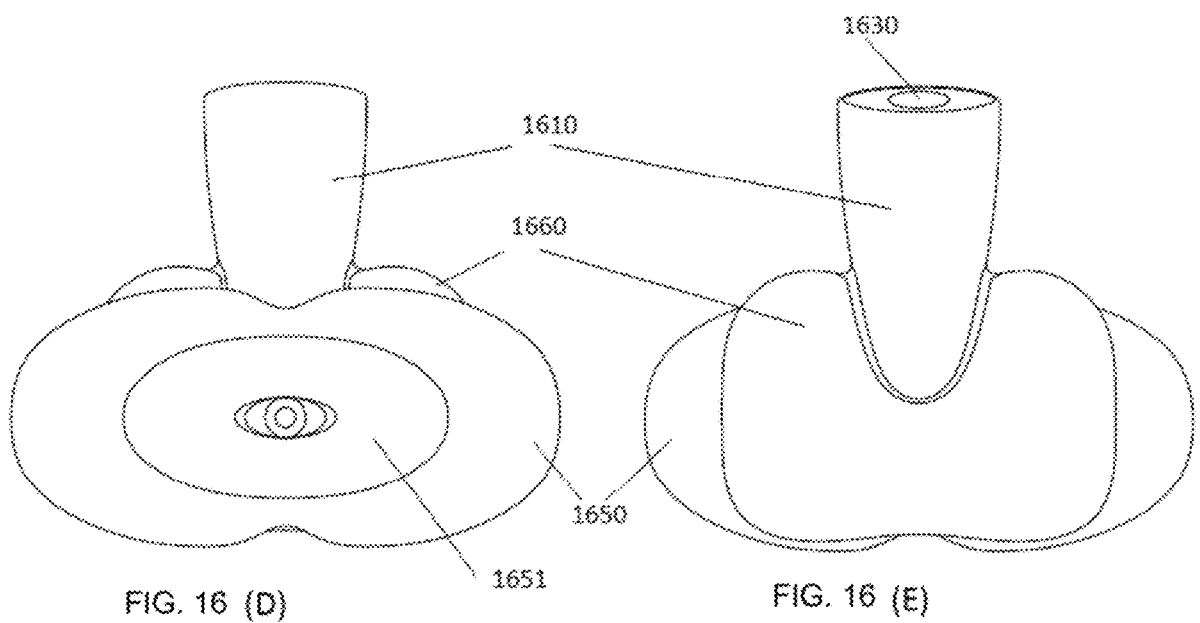
FIGS. 16A to 16E illustrate yet another aspect of the present invention showing various views of an exemplary oral device comprising a flexible tube and a tongue protector where the tongue protector is integrated on the flexible tube.

Referring now to FIGS. 11A to 11C, illustrate another aspect the present invention where an oral device 800 comprises a slidable flexible tube 810 with anchor points 880 in different positions. The oral device 800 further comprises a shield 850 with multiple anchor stops 870, which allow a patient to adjust the slide tube 810 to distinct positions (e.g., at W1, W2, W3). The oral device comprises a slidable flexible tube 810 and a shield 850 comprising a bendable middle part 851 where the flexible tube 810 passes through the shield 850. The flexible tube 810 further comprises at least one middle opening 840. The flexible tube 810 has an anterior end 820 to connect to a vacuum source and a posterior end 830 in place at the space between the tongue and the upper palate. The slidable flexible tube 810 allows a patient to adjust the position of the posterior end 830 to distinct positions (e.g., at W1, W2, W3) with anchor points 880 in different positions to provide a more comfortable or effective location to deliver negative pressure between the tongue and the upper palate. The flexible tube 810, in some embodiments, further comprises open channels 841 (e.g., shown at both sides of the flexible tube). The open channels 841 along the flexible tube 810 allow negative pressure distribution and prevent the middle opening 840 from obstruction by the soft tissue or tongue.

Referring to FIGS. 12A-12B, different views of a detachable tube part 901 having flexible tube 910 with open channels 941 will be described. In some embodiments, the flexible tube 910 comprises a bendable middle part 911. In certain embodiments, the middle part 911 is thinner than the rest part of the tube. In certain embodiments, the middle part 911 remains the same thickness as the rest part of the tube but still maintains the desired flexibility. The flexible tube 910 has an anterior end 920 to connect to a vacuum source and a posterior end 930 in place at the space between the tongue and the upper palate. The flexible tube 910, in some embodiments, has a wider structure near the posterior end 930 to provide rigidity of the tube, which prevent from collapsing due to being compressed by the tongue and the upper palate. In some embodiments, the posterior end 930 has a curved edge which decreases the risk of complete blockage by the soft tissue or tongue. The flexible tube 910 further comprises at least one middle opening 940 near an anchor stop 980. In some embodiments, the detachable tube part 901 has an outer surface 91 (see FIG. 12A) which contacts with an inner surface of the detachable shield pan to form a sealing interface to maintain negative pressure environment within oral cavity. The open channels 941 along, the flexible tube 910 allow negative pressure distribution and prevent the middle opening 940 from obstruction by the soft tissue or tongue. In some embodiments, the flexible tube 910 comprises at least one open channel, two open channels, three open channels, four open channels or more. The number of open channels is corresponding to the number of middle openings on the flexible tube. In certain embodiments, the flexible tube 910 comprises two open channels 940 connecting the middle openings 940 on two sides of flexible tube 910.

Referring to FIG. 13A, a flexible tube 1010 comprising at least one middle opening 1040 is shown in side view and top cross-section view. FIGS. 13B-13E further illustrate various embodiments of the present invention showing flexible tubes 1110 (FIG. 13B), 1210 (FIG. 13C), 1310 (FIG. 13D) and 1410 (FIG. 13E), with various designs of open channels 1141, 1241, 1341 and 1441, respectively. The open channels along the flexible tube allow negative pressure distribution and prevent the middle openings 1140, 1240, 1340 and 1440 from obstruction by the soft tissue or tongue. FIG. 13B shows that the open channel 1141 is located within the limitation of bendable part and does not extend to the posterior end. In certain embodiments, the open channels are extended to the posterior end of the flexible tubes (see the open channels 1241, 1341 and 1441 extended to the posterior end of the flexible tubes 1210, 1310 and 1410) where these sections of the flexible tube are solid, and therefore replace the function of the posterior end (1030 and 1130) to deliver negative pressure between tongue and upper palate (see e.g., FIGS. 13C to 13E). In some embodiments, as illustrated in FIGS. 13D and 13E, the flexible tube further comprises several support means 1342 or 1442 within the flexible tube to support the open channel from collapsing during the application of negative pressure. In some embodiments, the flexible tube comprises 1 to 20, 1 to 15, 1 to 10, 1 to 7, 1 to 6, 1 to 5, 1 to 4, 1 to 2, or one support means. The size and the position of the support means depend on the length of the open channel. One of ordinary skilled in the art would readily realize the suitable numbers with proper position and size to support open channels from collapsing when negative pressure applies to the flexible tube.

Referring to FIGS. 14A-F, another variation of the invention oral device comprising open channels connected with the posterior end without middle openings to deliver negative pressure from posterior part to anterior pan of oral cavity is shown in various views. The oral device shown comprises a shield 1450 to be situated between lips and front teeth, a tube passing through the shield, and a negative pressure deliverable part (i.e., a flexible tube 1410, which is part of or in connection with the tube passing through the shield), several open channels 1441 (e.g., two shown in the figures) connecting with the posterior end 1430 with indentation, and a tongue protector 1460, in some embodiments, as illustrated in FIGS. 13D and 13E, the flexible tube further comprises several support means within the flexible tube to support the open channel from collapsing during the application of negative pressure. In some embodiments, the flexible tube comprises 1 to 20, 1 to 15, 1 to 10, 1 to 7, 1 to 6, 1 to 5, 1 to 4, 1 to 2, or one support means. The size and the position of the support means depend on the length of the open channel. One of ordinary skilled in the art would readily realize the suitable numbers with proper position and size to support open channels from collapsing when negative pressure applies to the flexible tube.

Besides the flexible tube to accommodate different contours of the upper palate of patients, the oral device has fold lines 1454 (which are bendable) and recesses 1453 to allow the device conformable to different anatomy of jaws, front teeth and lips of different patients. The fold lines 1454 on the shield allow the shield to be pliable and compliant to the tooth orientations and shapes. The recesses 1453 near the joint where the tube passing through allows the flexible tube 1410 to bend freely. The indentation at the posterior end prevents the posterior end opening to be totally blocked by soft tissues. In this embodiment, there are no middle openings but yet the negative pressure is delivered from posterior part to anterior part of oral cavity via the open channels.

Referring to FIGS. 15A to 15E, another variation of the invention oral device comprising an extended tongue protector combining the function of tongue protection and a flexible negative pressure deliverable part is shown in various views. The oral device shown comprises a shield 1550 (which is disposed between the front teeth and the lips), a tube 1542 passing through the shield, an extended tongue protector 1560, one or more middle opening 1540 (e.g., one shown) near the center of the shield 1550 where the middle opening is connected to several open channels 1541 (e.g., three open channels shown). The flexible extended tongue protector covers both anterior and top regions of the tongue, which is pre-shaped to adapt (conform) the shape of upper palate (providing better fit of tongue shapes), thus allow patients to easily wear the oral device. The open channels on the extended tongue protector are connected to the middle opening (without posterior end openings) to deliver negative pressure from anterior part to posterior part of oral cavity. Multiple open channels distribute negative pressure more evenly.

Referring to FIGS. 16A to 16E, another variation of the invention oral device comprising a pre-bended flexible tube with an integrated tongue protector is shown in various views. These figures illustrate another embodiment where a tongue protector is connected with the flexible tube, not with the shield as described before. The oral device shown comprises a shield 1650 (which is disposed between the front teeth and the lips), a negative pressure deliverable part (i.e., a pre-bended flexible tube 1660) passing through the shield, a tongue protector 1660, where the tongue protector is integrated on the pre-bended tube. The pre-bended tube is shaped to adapt (conform) the shape of upper palate allowing patients to easily wear the oral device. The integrated tongue protector on the pre-bended tube adapts (conform) to tongue shapes allowing proper tongue protection.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. An oral device comprising:
a shield adapted to be inserted between lips and front teeth of a user, the shield having an anterior side and a posterior side; and
a tube passing through the shield from the anterior side of the shield through the posterior side of the shield, the tube defining a longitudinal lumen extending along the tube, wherein the tube is configured to fluidly connect an oral cavity of the user with a source of negative pressure to deliver negative pressure to the oral cavity via the longitudinal lumen,
wherein the tube has an anterior longitudinal portion extending outward from the anterior side of the shield and including an anterior end of the tube,
wherein the tube has a flexible posterior longitudinal portion extending outward from the posterior side of the shield and including a posterior end of the tube, the flexible posterior longitudinal portion defining a portion of the longitudinal lumen, the flexible posterior longitudinal portion being more flexible than the anterior longitudinal portion,
wherein the flexible posterior longitudinal portion and the posterior end are configured to be disposed between an upper palate and a tongue of the user and to conform to a contour of the upper palate of the user when the shield is inserted between the lips and front teeth of the user and negative pressure is delivered to the oral cavity via the tube.

2. The oral device of claim 1, wherein the shield is conformable to the shape of the front teeth and lips of the user.

3. The oral device of claim 2, wherein the shield is configured to seal the oral cavity when inserted between the lips and front teeth of the user.

4. The oral device of claim 1, wherein the shield includes at least one air vent configured to fluidly connect the oral cavity of the user to outside the user during use when the shield is inserted between the lips and front teeth of the user.

5. The oral device of claim 4, wherein the at least one air vent is located on the shield such that at least one of the lips of the user cover the at least one air vent when the shield is inserted between the lips and front teeth of the user.

6. The oral device of claim 4, wherein the at least one air vent comprises a one-way valve.

7. The oral device of claim 1, wherein the anterior end of the tube is configured to connect to a tube connected to the source of negative pressure.

8. The oral device of claim 7, in combination with the source of negative pressure fluidly connected to the anterior end of the tube.

9. The oral device of claim 1, wherein the shield has fold lines allowing the shield to be pliable and compliant to tooth orientations and shapes.

10. The oral device of claim 1, wherein the shield has recesses near a joint where the tube passing through allowing the tube to bend freely.

11. The oral device of claim 1, wherein the oral device further comprises a tongue protector to prevent direct impingement of teeth on a tip of the tongue of the user.

12. The oral device of claim 11, wherein the tongue protector is configured to be disposed between a bottom of the tongue tip and a back side of lower front teeth of the user.

13. The oral device of claim 12, wherein the tongue protector further comprises an indentation to accommodate a shape of a tongue frenulum of the user.

14. A system for eliminating air space in oral cavity comprising:
the oral device of claim 1; and
a negative pressure control system including a source of negative pressure, wherein the anterior end of the tube is fluidly connected to the source of negative pressure.

15. A method for eliminating air space in an oral cavity of a user, the method comprising:
attaching the oral device of claim 1 to the mouth of the user; and
delivering negative pressure the oral cavity of the patient via the tube to eliminate air space between a tongue and an upper palate of the user.

16. The oral device of claim 1, wherein the flexible posterior longitudinal portion has a first longitudinal section adjacent the shield and a second longitudinal section adjacent the posterior end of the tube, wherein the first longitudinal section is more flexible than the second longitudinal section, and wherein the posterior end of the tube comprises a free end of the tube that is the most posteriorly located portion of the tube.

17. The oral device of claim 1, wherein the tube is selectively movable relative to the shield in anterior and posterior directions to adjust a distance between the shield and the posterior end of the tube, and wherein the tube includes at least one anchor point and the shield includes at least one anchor stop, wherein the at least one anchor point is configured to selectively engage the at least one anchor stop to limit movement of the tube in the posterior direction.

18. The oral device of claim 17, wherein the at least one anchor point is configured to selectively engage the at least one anchor stop to further limit movement of the tube in the anterior direction.

19. The oral device of claim 1, wherein the longitudinal lumen in the flexible posterior longitudinal portion of the tube extends linearly from the shield to a free end of the tube.

20. The oral device of claim 1, wherein the flexible posterior longitudinal portion has a first longitudinal section adjacent the shield and a second longitudinal section adjacent the posterior end of the tube, wherein the second longitudinal section has a width greater than a width of the first longitudinal section.

21. The oral device of claim 20, wherein the first longitudinal section is more flexible than the second longitudinal section.

22. The oral device of claim 1, wherein the flexible posterior longitudinal portion includes opposite left and right side exterior surfaces extending along the flexible posterior longitudinal portion, and opposite upper and lower exterior surfaces extending along the flexible posterior longitudinal portion, wherein a width of the flexible posterior longitudinal portion extends between the left and right side exterior surfaces, wherein a thickness of the flexible posterior longitudinal portion extends between the upper and lower exterior surfaces.

23. The oral device of claim 22, wherein the flexible posterior longitudinal portion has a first longitudinal section adjacent the shield and a second longitudinal section adjacent the posterior end of the tube, wherein the width of the flexible posterior longitudinal portion at the second longitudinal portion is greater than the width of the flexible posterior longitudinal portion at the first longitudinal portion, and wherein the posterior end of the tube comprises a free end of the tube that is the most posteriorly located portion of the tube.

24. The oral device of claim 23, wherein the first longitudinal section is more flexible than the second longitudinal section.

25. The oral device of claim 23, wherein the flexible posterior longitudinal portion has a first longitudinal section adjacent the shield and a second longitudinal section adjacent the posterior end of the tube, wherein the thickness of the flexible posterior longitudinal portion at the second longitudinal portion is greater than the thickness of the flexible posterior longitudinal portion at the first longitudinal portion.

26. The oral device of claim 25, wherein the first longitudinal section is more flexible than the second longitudinal section.

27. The oral device of claim 25, wherein the width of the flexible posterior longitudinal portion at the second longitudinal portion is greater than the width of the flexible posterior longitudinal portion at the first longitudinal portion.

28. The oral device of claim 22, wherein at least one of the left and right side exterior surfaces defines a channel extending longitudinally along the flexible posterior longitudinal portion and through the posterior end of the tube.

29. The oral device of claim 28, wherein the posterior end of the tube defines an indentation fluidly connecting the channel to the longitudinal lumen at the posterior end of the tube.

30. The oral device of claim 22, wherein the left side exterior surface defines a left channel extending longitudinally along the flexible posterior longitudinal portion and through the posterior end of the tube, wherein the right side exterior surface defines a right channel extending longitudinally along the flexible posterior longitudinal portion and through the posterior end of the tube.

31. The oral device of claim 30, wherein the posterior end of the tube defines a left indentation fluidly connecting the left channel to the longitudinal lumen at the posterior end of the tube, wherein the posterior end of the tube defines a right indentation fluidly connecting the right channel to the longitudinal lumen at the posterior end of the tube.

32. The oral device of claim 1, wherein the flexible posterior longitudinal portion has an exterior surface defining at least one channel extending longitudinally along the flexible posterior longitudinal portion.

33. The oral device of claim 32, wherein the posterior end of the tube defines an indentation fluidly connecting the channel to the longitudinal lumen at the posterior end of the tube.

* * * * *